(12) United States Patent
Bunge et al.

(10) Patent No.: US 9,492,109 B2
(45) Date of Patent: Nov. 15, 2016

(54) MEDICAL SENSOR SYSTEM

(75) Inventors: Andreas Bunge, Leipzig (DE); Sarah Biela, Berlin (DE); Sven Bode, Berlin (DE); Joerg Naehring, Aachen (DE); Hoc Khiem Trieu, Westergellersen (DE); Gerald Urban, Freiburg (DE)

(73) Assignee: Biotronik SE & Co. KG (DE)

( * ) Notice: Subject to any disclaimer, the term of this patent is extended or adjusted under 35 U.S.C. 154(b) by 1425 days.

(21) Appl. No.: 13/253,121

(22) Filed: Oct. 5, 2011

(65) Prior Publication Data

US 2012/0088990 A1 Apr. 12, 2012

Related U.S. Application Data

(60) Provisional application No. 61/390,621, filed on Oct. 7, 2010, provisional application No. 61/412,802, filed on Nov. 12, 2010, provisional application No. 61/526,695, filed on Aug. 24, 2011.

(51) Int. Cl.
| | |
|---|---|
| *A61B 5/05* | (2006.01) |
| *A61B 5/145* | (2006.01) |
| *A61B 5/1473* | (2006.01) |
| *A61B 5/00* | (2006.01) |

(52) U.S. Cl.
CPC ....... *A61B 5/14546* (2013.01); *A61B 5/14503* (2013.01); *A61B 5/14735* (2013.01); *A61B 5/4839* (2013.01); *A61B 5/14539* (2013.01); *A61B 2562/0285* (2013.01)

(58) Field of Classification Search
CPC .......... A61B 5/14546; A61B 5/14735; A61B 5/4839; A61B 5/14503; A61B 5/14539
See application file for complete search history.

(56) References Cited

U.S. PATENT DOCUMENTS

| | | | |
|---|---|---|---|
| 5,840,083 | A | 11/1998 | Braach-Maksvytis |
| 6,527,762 | B1 | 3/2003 | Santini, Jr. et al. |
| 2001/0029348 | A1* | 10/2001 | Willis ................ A61B 5/14532 604/20 |
| 2003/0186914 | A1 | 10/2003 | Hofer et al. |
| 2004/0106858 | A1* | 6/2004 | Say .................... A61B 5/14532 600/345 |
| 2004/0200734 | A1* | 10/2004 | Co et al. .................... 205/777.5 |

(Continued)

FOREIGN PATENT DOCUMENTS

| | | |
|---|---|---|
| DE | 10 2006 025344 A1 | 12/2007 |
| DE | 10 2008 010 876 A1 | 9/2009 |

(Continued)

OTHER PUBLICATIONS

Vaidya et al., 2004, "Altering glucose oxidase to oxidase D galactose through crosslinking of imprinted protein", *ChemBioChem* 5 (1): 132-135.

(Continued)

*Primary Examiner* — Tiffany Weston
(74) *Attorney, Agent, or Firm* — Craig A. Fieschko, Esq.; DeWitt Ross & Stevens S.C.

(57) ABSTRACT

A medical sensor system (10, 10') for detecting at least one characteristic (12) of an human and/or animal body has a sensor (14), a first characteristic carrier (16), and a characteristic carrier receptor (18). The first characteristic carrier (16) differs, in terms of at least one characteristic parameter, from a second characteristic carrier (20) which is present at least at the time of detection. The sensor (14) is preferably located in vivo at the time of detection of the at least one characteristic.

21 Claims, 8 Drawing Sheets

(56) References Cited

U.S. PATENT DOCUMENTS

| | | |
|---|---|---|
| 2009/0061506 A1 | 3/2009 | Hofer et al. |
| 2009/0203980 A1* | 8/2009 | Carlson et al. ............... 600/365 |
| 2010/0193376 A1 | 8/2010 | Rius Ferrus et al. |
| 2010/0227382 A1 | 9/2010 | Lieber et al. |
| 2010/0280601 A1 | 11/2010 | Hofer et al. |
| 2011/0217697 A1 | 9/2011 | Rothberg et al. |

FOREIGN PATENT DOCUMENTS

| | | | |
|---|---|---|---|
| EP | 1 315 968 B1 | 6/2003 | |
| EP | 2 159 572 A1 | 3/2010 | |
| WO | WO 01/26708 * | 4/2001 | .............. A61M 1/00 |
| WO | WO 01/26708 A1 | 4/2001 | |
| WO | WO 2007137840 A1 | 12/2007 | |
| WO | WO 2008/154416 A2 | 2/2008 | |
| WO | WO 2008/143933 A2 | 11/2008 | |
| WO | WO 2010/008480 * | 1/2010 | ........... G01N 27/414 |
| WO | WO 2010008480 A2 | 1/2010 | |

OTHER PUBLICATIONS

Garcia A.J., 2005, Get a Grip, integrins in cell-biomaterial interactions; *Biomaterials* 26; 7525-7529.

Blindt et al., 2006, "A novel Drug-Eluting Stent coated with an Integrin-Binding Cyclic Arg-Gly-Asp Peptide Inhibits Neointimal Hyperplasia by Recruiting Endothelial Progenitor Cells"; *JA College of Cardiology*; vol. 47, No. 9, 1786-1795.

Albu et al., 2007, "Self-organized, free-standing TiO2 nanotube membrane for flow-through photocatalytic applications," *Nano Lett.* ,7(5):1286-9 (Epub Apr. 25, 2007).

Saerens et al., 2008, "Antibody Fragments as Probing in Biosensor Development", *Sensors*, 8, 4669-4686.

* cited by examiner

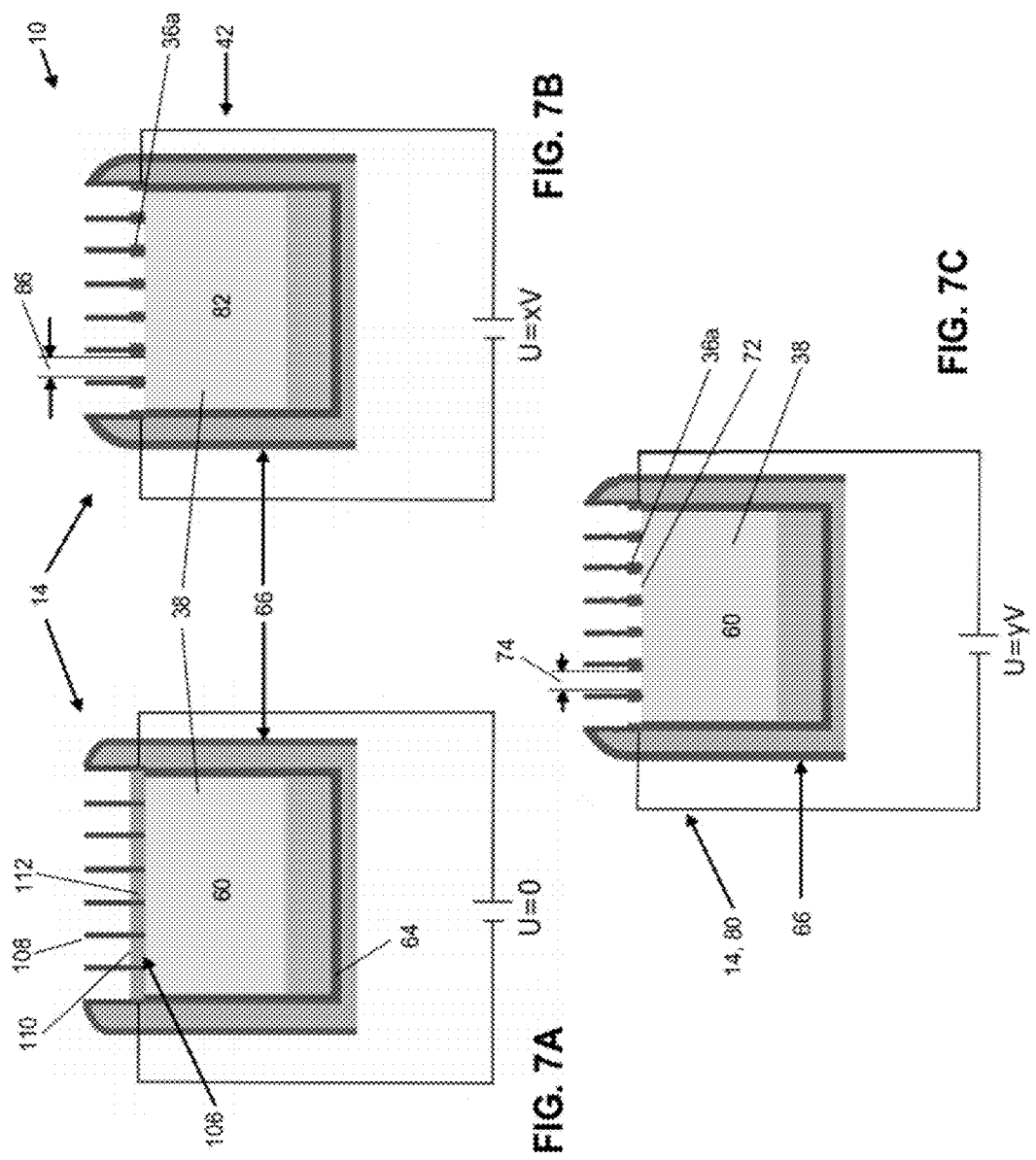

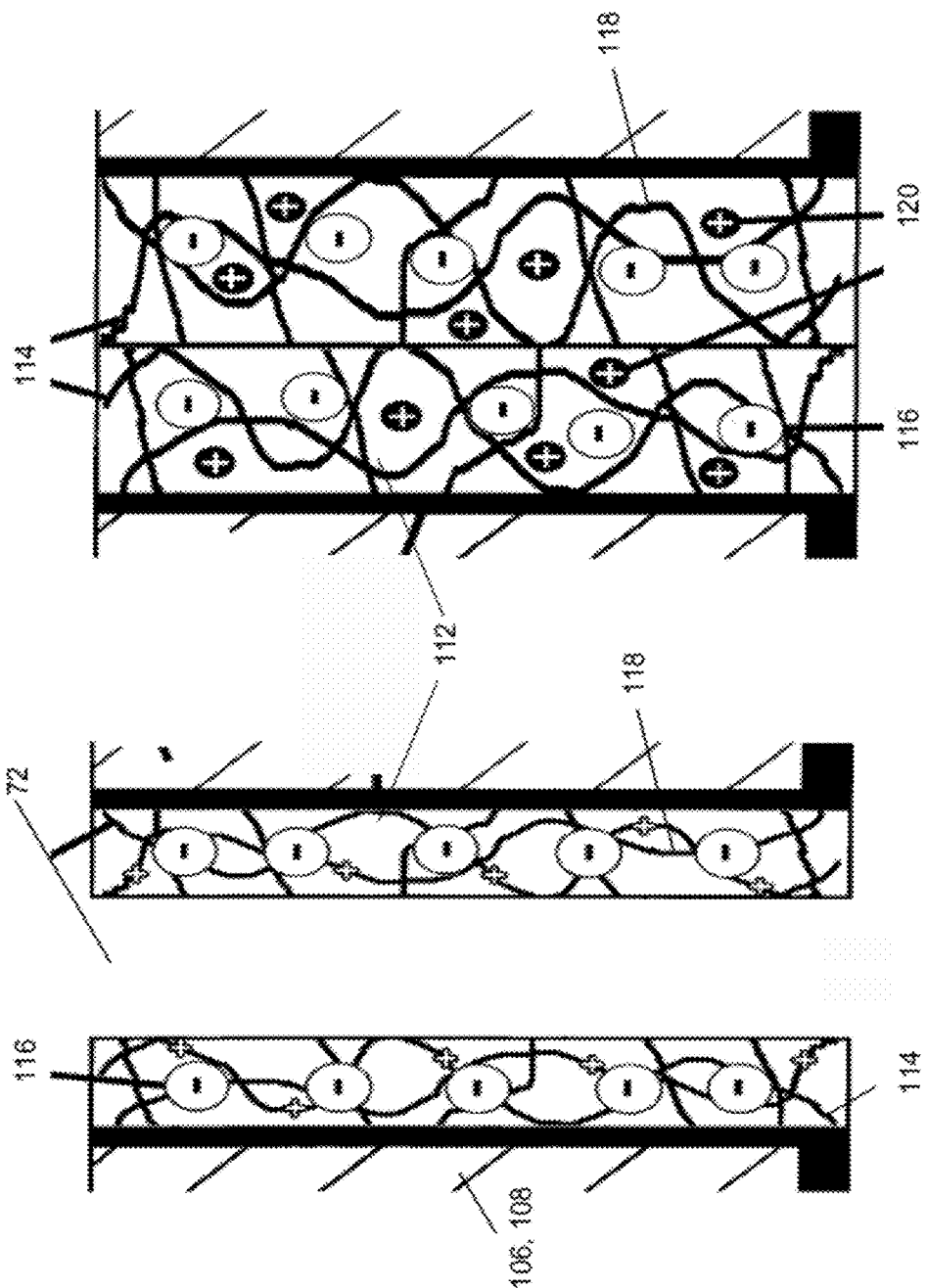

MEDICAL SENSOR SYSTEM

CROSS-REFERENCE TO RELATED APPLICATIONS

This application claims priority under 35 USC §119(e) to U.S. Provisional Patent Application 61/390,621 filed Oct. 7, 2010; U.S. Provisional Patent Application 61/412,802 filed Nov. 12, 2010; and U.S. Provisional Patent Application 61/526,695 filed Aug. 24, 2011. The entireties of these prior applications are incorporated by reference herein.

FIELD OF THE INVENTION

The invention relates to a medical sensor system and a method for operating such a system according to the preambles of the independent claims.

BACKGROUND OF THE INVENTION

Proteins are a medically relevant class of substances which are involved in many important processes in the body, e.g., as enzymes, as means for transporting other molecules, and as clotting factors in the blood. It is particularly useful, especially in the case of disease, to detect such proteins or the quantities or concentrations thereof, for example, in the blood. Chemical, enzymatic, optical, and other methods of diagnostic testing are used for this purpose. Proteins have a three-dimensional structure, which is defined by their amino acid sequence and used by the immune system, through specific antibody recognition, wherein antibodies are able to distinguish between foreign proteins and their own proteins. This interaction between the antibody and the so-called antigen can be used as an immunological assay, and has become the established standard method used in in vitro diagnostics.

This principle is also applied in a "competition assay" to determine the concentration of an antigen. In this case, at the start of the test the antibodies are provided with antagonists that bind to the antibody, for example, wherein the antagonists bear a fluorescent labeling, whereby an optical measurement signal is generated. In the presence of the substance to be detected—an analyte—some of the fluorescent labeled antagonists are displaced from the binding site of the antibody by the analyte. As a result, the number of antibodies having fluorescent labeling is decreased, and therefore, a smaller measurement signal is derived. This simplest form of competition assay involves a purified or recombinantly produced labeled antigen, which is present together with the binding antibody as an antigen/antibody complex. The unlabeled antigen (analyte) to be measured binds to the antibody with the same affinity and replaces the labeled molecule to a certain extent. If the equilibrium constant of the reaction is known, the concentration of unmarked antigen can be to determined from the measurement of the replacement.

Also known are in vitro methods for molecule detection without optically measurable labeling. In this case, field effect transistors (FET) are used in vitro, for example. These approaches involve the molecule to be detected reaching a sensitive layer of the FET as a result of diffusion. For this to occur, the molecule must carry a charge in order for the charge transfer that is necessary for detection to take place. Alternatively, catcher molecules (e.g., antibodies) can be immobilized on the sensitive layer of the FET, which molecules are able to recognize, bind to, and concentrate specifically the analyte to be detected. The binding of the analyte to the antibody layer results in the charge transfer.

Over the past several decades, it has been found that an in vitro assay of analytes is often insufficient for a reliable determination of a current and relevant status of the analyte, and is thus insufficient for a reliable determination of a condition of a patient. Rapid intervention is essential, particularly in the event of acute changes in chronically ill patients, for example. In such cases, continuous monitoring of analytes and concentrations thereof over months or even years is recommended. Therefore, a sensor system is needed which is capable of reliably and rapidly monitoring analytes, for example, in vivo over an extended period of time.

The currently known sensor systems are unsuitable for in vivo applications. An antibody or competition assay, as described above, can ordinarily be used only a single time in a detection process because the antibodies bind so securely to their specific antigen, and the formed bond cannot be easily separated. An assay of this type does provide a highly precise, but single measurement of the concentration of the substance during one moment in time. However, in order to monitor a concentration of analyte over a period of months/years it is necessary for the bond between antibody and analyte to be reversible, so that in addition to providing a single instantaneous measurement, the assay can also detect varying concentrations. Moreover, the antibodies used for this purpose are not particularly stable under long term contact with bodily fluids.

In addition, most optically active labels are hazardous to a patient's health or even toxic, particularly if they escape from the sensor system (for example, as a result of decomposition processes) and enter the body, where they can evoke critical reactions and/or inflammatory reactions. This also results in a depletion of detection molecules and a deactivation of the optically active labels, for example, as a result of photobleaching, thereby impairing the functionality of the sensor system. In addition, for antibody detection methods, several washing steps are typically required for eliminating unbonded or interfering molecules. For an implantable sensor having an assay as described above, this would require a microfluid system and therefore a significant enlargement of the implant (including a rinsing reservoir), which would be unreasonable for implantation into a patient.

The molecules that are typically detected using FET's are highly charged polyelectrolytes, such as DNA, for example. However, under physiological conditions most proteins carry a very low charge and cannot routinely be detected using an FET unless special labels, such as nanoparticles, which often pose a health hazard, are used to amplify the signal.

Heretofore, only pH sensors and blood gas sensors (electrodes) have become established as reliable electrical methods for detecting a condition of the blood. These sensors are used mostly in intensive care units, in which case continuous access to the patient's blood via shunts and catheters is required. A sensor system of this type is not suitable for continuous use over a period of months or years.

Therefore, there is no currently known fully implantable sensor system that will remain stable over the long term, and which is capable of monitoring and determining the concentration of larger analytes (such as proteins) over a period of months or even years. No approaches are known which describe a fully implantable detection system for proteins on the basis of antibodies. Heretofore, only in vitro systems which cannot be used in vivo are known.

SUMMARY OF THE INVENTION

The invention involves a sensor system and a method for operating the system, which will allow a status parameter of a human and/or animal body to be monitored reliably, continuously, and without disruption, over an extended time period, and preferably over a period of months or years.

A medical sensor system for detecting at least one characteristic of a body (e.g., a human or animal body) includes at least one sensor, at least one carrier of the characteristic (e.g., a first characteristic carrier), and at least one receptor for the characteristic carrier, wherein the first characteristic carrier differs in terms of at least one characteristic parameter from a second characteristic carrier that is present at least at the time of detection.

The sensor is preferably located in vivo during the detection of the characteristic(s), whereby the characteristic(s) can be monitored particularly closely. Moreover, acute changes can be detected rapidly and countermeasures initiated equally rapidly. In addition, detection does not place undue strain on the patient, since the only invasive treatment involved is the implanting of the sensor system into the body.

In this context, a "sensor system" is understood as a system having at least one sensor. The sensor system may also have additional components, such as additional sensors, a housing, electronic components, a power supply, a telemetry unit, a control unit with an electronic evaluation system, an anchoring unit, and/or any other component deemed relevant by a person skilled in the art.

A "characteristic" is understood as a parameter such as a pH value, an osmolality, a charge of an ion, a polyelectrolyte or a protein, for example, a temperature, a configuration of a binding site, for example, a size, a mass, a state of aggregation, the water content, the hematocrit value, the partial thromboplastin time, the plasma thrombin clotting time, the Quick's value, a presence and/or absence and/or a quantity of a substance and/or an analyte, and/or any other parameter deemed relevant by a person skilled in the art. Preferably, the characteristic is a charge and/or is a measurement of a quantity and/or a concentration of an analyte. In this context, a "characteristic parameter" is understood as a feature of the characteristic, for example, acid, basic, high, low, cold, warm, hot, strong, weak, a degree of intensity and/or any other feature deemed relevant by a person skilled in the art. In this case, it is clear to a person skilled in the art that a characteristic parameter of a characteristic is always relative to another characteristic parameter of the characteristic.

An "analyte" is, for example, an electrolyte, a fat, a salt, an ion, a polyelectrolyte, a carbohydrate, a fatty acid, a lipid, a sugar, a nucleotide, a deoxyribonucleic acid, a ribonucleic acid, an amino acid, a peptide, a protein, an antibody, a hormone, a neurotransmitter, a metabolite, a catabolite, an antigen, an enzyme, a drug, a nanoparticle, a toxin, water, and/or any other substance deemed relevant by a person skilled in the art. A "characteristic" also encompasses so-called biomarkers, which form a variable constituent of the human or animal body, such as albumins/globulins, alkaline phosphatase, alpha-1-globulin, alpha-2-globulin, alpha-1-antitrypsin, alpha-1-fetoprotein, alpha-amylases, alpha-hydroxybutyrate dehydrogenase, ammonia, antithrombin III, bicarbonate, bilirubin, carbohydrate antigen 19-9, carcinoembryonic antigens, chloride, cholesterol, cholinesterase, chylomicron residues, cobalamin/vitamin B12, ceruloplasmin, C-reactive proteins, cystatin C, D-dimers, iron, erythropoietin, erythrocytes, ferritin, fetuin A, fibrinogen, folic acid/vitamin B9, free tetraiodothyronine (fT4), free triiodothyronine (fT3), gamma-glutamyl transferase, glucose, glutamate dehydrogenase, glutamate oxaloacetate transaminase, glutamate pyruvate transaminase, glycohemoglobin, hematocrit, hemoglobin, haptoglobin, uric acid, urea, HDL cholesterol, homocystine, immunoglobulin A, immunoglobulin E, immunoglobulin G, immunoglobulin M, INR, potassium, calcium, creatinine, creatinine kinase, copper, lactate, lactate dehydrogenase, LDL cholesterol, leucocytes, lipase, lipoprotein, magnesium, corpuscular hemoglobin, myoglobin, sodium, NT-proBNP/BNP, phosphate, prostate-specific antigens, reticulocytes, rheumatoid factor, thrombocytes, thyroid stimulating hormone, transferrin, triglycerides, troponin T, and VLDL-cholesterol.

A "characteristic" is also understood as an "active ingredient," wherein the term "active ingredient" includes typical drugs or even metabolites that are administered for the treatment of diseases, such as muscarine receptor antagonists, neuromuscular blocking substances, cholesterase inhibitors, adrenoceptor agonists, indirect sympathomimetics, methylxanthine, alpha-adrenoceptor antagonists, ergot alkaloids, beta-adrenoceptor antagonists, deactivation inhibitors, antisympathonics, 5-HT-receptor agonists, histamine receptor agonists, histamine receptor antagonists, analgesics, local anesthetics, sedatives, anticonvulsives, convulsives, muscle relaxants, anti-Parkinson drugs, neuroleptics, antidepressants, lithium, tranquilizers, immunosuppressants, antirheumatics, antiarrhythmics, antibiotics, ACE inhibitors, aldosterone receptor antagonists, diuretics, vasodilators, positively inotropic substances, antithrombotic/thrombolytic substances, laxatives, antidiarrheals, drugs used for adiposity, uricostatics, uricosurics, lipid reducers, antidiabetics, antihypoglycemics, hormones, iodine salts, thyrostatics, iron, vitamins, trace elements, virostatics, antimycotics, antituberculotics and substances used in chemotherapy treatment of tumors. Preferably, the characteristic relates to a variable constituent of the human and/or animal body. Many such analytes can be assayed in a bodily fluid, such as lymph, bile, urine, tears, saliva, liquor, interstitial fluid and/or particularly blood, in order to determine the clinical status of individual patients, particularly those suffering from chronic illness, such as cardiac insufficiency and renal insufficiency, for example. In a preferred version of the invention, the sensor system is used to detect a member of the cystatin family of cysteine protease inhibitors, and more particularly to detect cystatin C, and is therefore a cystatin C sensor.

Further, a sensor is particularly understood as a component that is capable of qualitatively and/or quantitatively detecting an optical, physical, chemical and/or electrochemical property of the characteristic (for example, as a measured variable) in an area surrounding the sensor. Moreover, the second characteristic carrier may be defined by an analyte, for example, and the first characteristic carrier may be defined by another analyte, particularly an opponent and/or an antagonist of the analyte. The characteristic and the second characteristic carrier can also be the same object or molecule, particularly if the characteristic is assayed on the basis of the presence or absence of the second characteristic carrier/analyte. In addition, the second characteristic carrier or the analyte is present at least at the time of detection at the sensor, but may also be present at other times, for example, when the sensor system is in rest mode. The receptor for the characteristic carrier can be formed generally, for example, by peptides, antigens, aptamers, molecularly imprinted polymers and polynucleotides with $n \geq 1$ monomer units (ribonucleic acid or RNA, deoxyribonucleic acid or DNA, peptide nucleic acid or PNA, locked nucleic acids or LNA) or more particularly by a receptor, a channel, a transport protein and/or particularly by an antibody or a part of an antibody.

Advantageously, the sensor detects at least one electrical status variable, such as a resistance, a current, and/or (preferably) a voltage. With this measurement principle, a sensor system can be provided which has a small space requirement and low energy use. It is further proposed that the sensor detects at least one change in voltage. This change in voltage is brought about by a difference in charge between the first characteristic carrier and the second characteristic carrier, whereby the sensor is a charge-sensitive sensor. With this type of determination, a highly sensitive system can be produced.

A further advantage is that the sensor has at least one semiconductor component, such as a FET (field effect transistor)-based active component, a seFET ("extended gate" field effect transistor), an ISFET (ion-sensitive field effect transistor), an EPROM (electrically erasable programmable read only memory) or an EEPROM (electrically erasable programmable read only memory), a capacitor, a nanotube, a nanowire and/or any other semiconductor component deemed appropriate by a person skilled in the art. Alternatively or additionally, an impedimetric system may be used in the sensor. Such components allow the sensor system to be implemented particularly easily in a miniaturized format.

At least one region of the sensor is preferably coated with at least the characteristic carrier receptor. This region is preferably formed by a region that is relevant to measurement and/or by an active sensor surface, and particularly preferably has a so-called "floating gate", and/or the region is formed by the gate. The region is further coated with characteristic carrier receptors, wherein their density is dependent on characteristics of the first and second characteristic carriers and the characteristic carrier receptor that is used. Appropriate densities for characteristic carrier receptors can be defined by a person skilled in the art according to his knowledge in the field, and/or in accordance with experimental refinement of the receptor density. In addition, the characteristic carrier receptor can be bound to the surface by means of a linker, such as polyethylene glycol, protein A, or protein G. In this context, linkers can also be smaller organic molecules, such as EDC, individual amino acids or generally short polypeptides having a length of n=6-12 (n being the number of bonded amino acids). In this manner, the charge transfer from the first characteristic carrier bound to the characteristic carrier receptor can be transferred in a structurally simple manner to the semiconductor component or the "gate" thereof.

A widely applicable sensor system can be achieved if the system includes a competition assay. In this case, the characteristic carrier receptor is formed by a molecule that has an antigen recognition site, in other words an antigen binding partner, such as a polyclonal or monoclonal antibody, for example. In this manner, a specific and selective interaction with the antigen can be easily achieved in a structurally simple manner. For this purpose, it is proposed that the second characteristic carrier is formed by an analyte having an antigen. In addition, the first characteristic carrier is formed by an antagonist of the analyte, which also has the antigen. In what follows, the terms second characteristic carrier and analyte, and first characteristic carrier and antagonist, will be used synonymously. The antagonist is an artificially produced or modified molecule, particularly recombinant, which has the same molecular antibody recognition site as the analyte. This recognition site can be established, for example, by means of molecular engineering and by epitope mapping with subsequent recombinant gene cloning and protein expression. In this case, a precise determination of a molecular antibody/antigen interaction site is carried out based upon the amino acid sequences of the antibody and the antigen. In addition, the first characteristic carrier or the antagonist has a higher charge than the second characteristic carrier or the analyte. This high charge is achieved by coupling molecules that have a high charge to the modified antagonist. These molecules are, for example, anionic or cationic polymers, such as heteropolypeptides or homopolypeptides. In this case, poly-L-lysine would be preferably usable. As a result of this modification, the first characteristic carrier bears not only a high charge, but also a high volume, and thus it can be advantageously retained inside a sensor. Because the antagonists can be designed relatively freely through recombination/bioinformatics, a high signal-to-noise distance can be achieved with displacement, without modifying the actual analyte, thereby enabling sensitive measurement. The high charge density of the aforementioned antagonist can be achieved, for example, through recombinant cloning. For example, for detecting cystatin C, an additional protein portion can be recombinantly added to a suitable base sequence, which portion will not modify the required antibody binding site and preferably consists of an amino acid, which carries a charge. Suitable amino acids that carry a charge are lysine, arginine and histidine, and aspartate (as the ionized form of asparaginic acid) and glutamate as the ionized form of glutamic acid, both of which are negatively charged at pH-levels above 5.

The principle of the sensor is based upon a label-free immunological detection method in which an endogenic biomarker molecule is reversibly measured on the basis of concentration. The sensor system therefore operates using a particularly sensitive method based upon an immunological competition assay for detecting and/or for determining the concentration of the analyte in conjunction with its antagonist and the antigen binding partner thereof. The surface of the sensor has the bound characteristic carrier receptors that selectively recognize the analyte. In the absence of the analyte, the antagonists present inside the sensor saturate the active surface of the sensor by binding the characteristic carrier receptors. The high charge of the antagonist produces a measurable charge transfer on the sensitive surface of the semiconductor component, thereby generating a reliable, drift-free measurement signal, which can nevertheless be corrected if necessary, on the seFET. Saturating the measuring sensor with the antagonist causes the measurement signal to be 100% when the analyte is absent.

If the analyte is present on the active surface, antagonist and analyte compete for the antigen recognition side of the antigen binding partner. This results in a reversible displacement of the antagonist provided with a high charge, which is bound to the antigen binding partner, by the actual antigen of the analyte. A concentration-dependent equilibrium develops between bound analyte and bound antagonist, wherein the charge transfer for the analyte and antagonist is different. Overall, the more analyte that is bound, the lower the measurement signal that can be derived. As a result of the significant charge difference between analyte and antagonist, the change in the concentration is clearly detectable, and the desired principle of measurement amplification is applied. The analyte concentration is proportional to the measured signal. If the concentration of analyte in the blood, and therefore also inside the sensor, drops, then primarily antagonists again bind to the characteristic carrier receptor, and the measurement signal at the seFET again increases.

Because all the binding energy is provided by the recognition sequence in the antigen, a change in mass between two mutually displaced molecules does not play a decisive role in measurement if there is sufficient distance between the molecules. Generation of the reference signal inside the sensor itself (in the absence of the antigen) also provides a reference point for measurement, in order to allow calculation of sensor drift or gradual sensor degradation (as a result of autolysis of the molecules, degradation of the measuring sensor coating in the seFET, or effects of the body on the implant). The saturation of the measurement sensor with the antagonist in the absence of the analyte may necessitate an internal drift correction of the measuring sensor, because with unavoidable gradual sensor degradation, the maximum potential measurement signal is gradually decreased, even without the presence of the analyte. In the electronic system of the measuring sensor, this gradual, concentration-independent signal decrease can be detected and eliminated in the form of a drift correction based on empirical data.

The problems that most analytes (e.g., proteins) carry only low charges that are difficult to detect, and that previous charge-sensitive detection methods have not been sensitive enough for such small molecules with low charges, can be solved by using a competition assay and an antagonist that carries high charges. The displacement of the antagonist having a high charge by the analyte having a low intrinsic charge makes the change in the analyte concentration very clearly measurable, since the high charge of the antagonist in the analyte-free condition results in a signal amplification. In addition, the competition assay increases the sensitivity of the seFET, since the displacement of the highly charged antagonist by the analyte causes the measurement signal to change very significantly. This further leads to an improvement in the signal-to-noise distance. Moreover, interference effects of small charged molecules and materials in the measuring substance are decreased, since any non-specific interactions produce only a very low difference in charge as compared with the displacement of the highly charged antagonist. A sensor system of this type can also be configured to save energy and space, which makes it particularly well suited for in vivo use and for monitoring purposes.

The measuring method must be fully reversible within a short period of time, so that the to sensor will be "reusable" and can be used for an extended period of time. For this purpose, the characteristic carrier receptor or the antibody must be configured as a conventional antibody with high specificity but low affinity for the antigen. In addition, it must bind the analyte and the antagonist in equilibrium, dependent on the concentration of the analyte in the measuring medium. It is known that antibody fragments (artificially modified, reduced-size antibodies) have the same specificity but a lower affinity for an antigen than unmodified antibodies, and can therefore be used more easily in the sensor system (cf., Saerens et al., "Antibody Fragments as Probing in Biosensor Development", Sensors 2008, 8, 4669-4686). It is further known that antibody fragments trigger human immune reactions much more rarely than whole antibodies, since particularly those regions that are irrelevant to binding but are immunogenically constant are readily deleted.

The characteristic carrier receptor can be, for example, a part of a polyclonal or monoclonal antibody, such as a Fab fragment, an scFv fragment, an hsFv fragment, a dsFV fragment, a ds-scFc fragment, or a VH or VL domain. (For a summary of potentially usable antibody fragments, domains and modifications, see Saerens et al.) The antigen-antibody bond should be relatively weak in this case, and the affinity of the antibody or the antibody fragment should be in about the μ-molar range. The binding constant of the antibody bond should advantageously be less than $1\times10^{-9}$ mol/l, preferably less than $5\times10^{-8}$ mol/l, particularly preferably about $1\times10^{-8}$ mol/l. The bond strength of the antibody or antibody fragment can be influenced by selection both during isolation and during recombinant optimization. The methods used for this purpose are standard methods of molecular biology (e.g., phage display, peptide display). The final characteristic carrier receptor is artificial. Due to the lower affinity of the antibody fragments for the analyte and the antagonist (as compared with traditional antibodies), the bond between the binding partners is reversible, and therefore, measurable equilibrium states can be rapidly established and adjusted. Thus washing steps in the antibody assay can be avoided, thereby permitting a miniaturization of the sensor system and implantation.

In addition, the antibodies or antibody fragments are configured to be stable over the long term, as it is preferable to have a substantially greater long-term stability as compared with classic antibody detection methods. Therefore, in a further version of the invention it is proposed that the characteristic carrier receptor and/or the first characteristic carrier are chemically, biologically and/or genetically modified or "hardened." This involves particularly regions of the molecules that are irrelevant to the binding of the antigen and the antagonist. Any such chemical modification is preferably one that does not affect binding. For effective long-term stability, antibody fragments must be prepared that are stable against proteases and chemical degradation, for example (cf., Saerens et al.). Possibilities for modification include:

1. Removing unnecessary constituents of the protein (genetic modification),
2. Removing known protease interfaces in the protein (genetic modification), such as the removal or exchange of the amino acid serine or other individual amino acids in specific amino acid sequences, which prevents the attack on and degradation of the protein by serine proteases, for example,
3. Incorporating "non-physiological" amino acids into the antibodies which cannot be attacked in the "host system" (expression of the protein in heterologous systems),
4. Special secondary modifications to the antibody surface which cannot be attacked by the host system (alternative glycosylation), such as methylations, for example, which are capable of preventing the attack of certain proteases or the spontaneous degradation of amino acids,
5. Chemical modification (e.g., targeted oxidation), which inhibits or impedes degradation under physiological conditions.

The possible modifications are also dependent on the requirements for the antibody or the antibody fragment, and for the antagonist. Not all modifications are necessary at the same time, and selected modifications can be used as desired. Positive results can generally be achieved by using only options 1 and 2 above. By modifying the antibody or the antibody fragment and the antagonist, these can be made stable over the long term, in contrast to conventional biomolecules, and can be active over an extended period of time in the sensor, as well as tracking and detecting changes in the analyte concentration.

It can further be advantageous for the sensor system to have at least one organic membrane, by means of which at least one reservoir of the sensor can be closed off. In this context, the term "organic membrane" is understood as a dividing layer and/or a thin film, which has at least one constituent that is based on a carbon compound. The organic membrane preferably contains a polymeric substance and/or is formed by a polymeric substance, wherein the substance can be produced chemically in such a way that the pore size of pores of the membrane is adapted to the molecules and the measuring principle that are used. The membrane is preferably embodied as a semipermeable membrane. The term "closed off" in this context does not necessarily mean that the transport of substance between the reservoir and an external region is entirely prevented, and instead means merely that a space is defined in which certain components of the sensor system are located and/or retained. A "reservoir of a sensor" or a "sensor reservoir" in this case is understood as a space, a chamber and/or a cavity of the sensor, with which the detection system of the sensor is in contact and/or on and preferably in which the detection system or the competition assay is located. A base of the reservoir, opposite the semipermeable membrane, preferably has the "gate" of the semiconductor component or of the seFET. The sensor reservoir further encloses at least one volume, particularly a sample volume, which can contain or have the characteristic that is to be detected. The organic membrane can advantageously be used to determine which molecules can come into contact with the sensor, and which cannot. The membrane and the sensor are connected to the housing of the sensor in such a way that an exchange of substance is possible only via the pore membrane and not via the connection site between pore membrane and housing.

The organic membrane is preferably formed such that the first characteristic carrier or the antagonist can always be retained in the reservoir, thereby preventing loss of a constituent of the assay in a structurally simple manner. In addition, negative effects of the release of the antagonist into the body of the patient are prevented. The organic membrane is further formed such that it is at least temporarily passable by the second characteristic carrier or the analyte. The semipermeable membrane, which filters the analyte into the interior of the sensor, but does not allow the charge carrying antagonist to pass out, results in a reusable sensor that is stable over the long term, thereby permitting miniaturization and therefore implantation. In addition, molecules such as other blood constituents, for example, which are larger than the pore size of the membrane, are prevented from entering the reservoir, and therefore interfering effects can be excluded. In this manner, a signal-to-noise ratio can be realized that is low enough that a sufficiently high measurable signal can be detected. Furthermore, washing steps can thereby be eliminated, which would otherwise result in an unreasonable sensor and/or implant size.

The organic membrane is preferably controllable, wherein "controllable" is understood to mean that the membrane can be converted from at least one selected initial state to at least one selected final state by means of at least one signal. Advantageously, the signal is a factor acting from outside the sensor system, such as radiation, infrared, ultrasound, an electrical field, a magnetic field, visible light, a protein, a peptide, a polyelectrolyte, a pH level change, a change in ion concentration, a change in temperature, and/or any other factor deemed suitable by a person skilled in the art. Preferably, a volume of the membrane can be controlled by an electrical signal.

The controllable organic membrane is also preferably adjustable, either continuously (steplessly) or discretely (in stages), between an opened and a closed state of the reservoir. In this context, "stepless" is understood as the ability to adjust the opening width of the membrane continuously to a maximum limit, or to any width. The adjustment is preferably reversible. By implementing this change, the detection system located in the sensor reservoir can be advantageously protected against interfering molecules, which could attack, degrade, and/or destroy the sensor. In addition, interfering factors that can impair the trouble-free functioning of the sensor are thereby advantageously minimized. In this manner, a sensor system having a particularly long lifespan can be produced. A suitable controllable organic membrane is described, for example, in DE 10 2008 010 876 A1.

It is further useful for the controllable organic membrane to be closed prior to a first use or a first measuring operation by the sensor, thereby effectively protecting the sensor against interfering influences, such as dirt, dust, excess moisture, dryness, temperature fluctuations and/or harmful molecules, before it is first placed in use. It can also be advantageous for the controllable, organic membrane to be closeable between the individual measurements, thereby allowing the sensor system components to be stably implemented.

The organic membrane has at least one pore, the diameter of which is reversibly adjustable, thereby allowing a condition of the membrane and a transfer of the analyte into the sample volume to be configured in a particularly structurally simple manner, particularly for different molecules and/or analytes. Moreover, at least an opening and/or a closing of the pore of the membrane can be controlled. The pore is preferably a nanopore, and the pore diameter is dependent upon the analyte to be detected. The pore diameter is preferably chosen such that the membrane is permeable to molecules of the analyte, but acts as a barrier to larger molecules. If the analyte to be detected is a protein or an analyte of similar size, the pores can generally have a maximum diameter of 1 μm, preferably a maximum of 250 nm, more preferably a maximum of 100 nm, advantageously a maximum of 50 nm and particularly preferably a maximum of 10 nm. In the case of smaller analytes, the pores can have a maximum diameter of 500 nm, preferably a maximum of 100 nm, more preferably a maximum of 50 nm, advantageously a maximum of 10 nm and particularly preferably a maximum of 1 nm. In general, the pore can also have any other shape, such as triangular, rectangular, star-shaped, oval and/or any other shape deemed expedient by a person skilled in the art, wherein the maximum dimension is as discussed above. With the nanopore, structures such as cells, large molecules or molecule aggregates, which are larger than the diameter of the nanopore can be easily prevented from penetrating into the sample volume from the area surrounding the sensor, where they could disrupt the detection system. Advantageously, the membrane has a plurality of similar pores, which are evenly distributed over a surface of the membrane. In principle, a non-homogeneous distribution of the pores would also be usable. Advantageously, the pore diameter can be adjusted steplessly or in stages, allowing it to be used with a plurality of analytes.

The controllable organic membrane advantageously has at least one material having an adjustable redox status. The redox status can be adjustable chemically, electrically and/or in any other manner deemed suitable by a person skilled in the art. Advantageously, the controllable organic membrane can change its status on the basis of the initiating signal in such a way that at least a part of the membrane is permeable to the analyte, thereby providing the analyte with good access to the detection system.

The organic membrane is preferably formed to be electrically controllable, more particularly, the pore diameter of the pore(s) of the membrane are electrically controllable. This is preferably accomplished by applying a maximum voltage of approximately 2 V. When the nanopores are fully opened, the material that is capable of adjusting its redox status is at its minimum volume. Applying a voltage leads to an increase in the volume of the material, thereby reducing the open diameter. The increase in volume is dependent on the level of the voltage, or if the voltage is applied for a certain amount of time, or is dependent on the time span during which a constant voltage is applied. Reversing the process is accomplished similarly by applying a voltage of reverse polarity, which then leads to a decrease in the volume of the material. The change in volume is also dependent on the structural design of the material.

Preferably, the material that is capable of changing its redox status is an electroactive material or an electroreactive polymer. If a mixture of polypyrrole (PPy) and dodecyl benzene sulfonate (DBS) is used as the electroactive polymer, for example, then during a voltage-controlled reduction of the polymer, sodium ions are inserted into the polymer. This insertion of sodium ions produces a highly lateral change in the volume of the electroactive polymer, thereby closing the pores to the analyte. The reversibility of this process enables a controlled opening and a controlled closing of the pores, and thereby a controlled, repeatable measurement by means of the sensor. Over the degree of reduction of the polymer, a partial volume change of the polymer is possible. The redox statuses of the electroactive polymer are generated by means of different applied voltages, and are maintained when the voltage is shut off. In this manner, the polymer and therefore the pore diameter can be advantageously adjusted to analytes of different sizes. Other substances may be used as an alternative to polypyrrole (PPy) in the above-described electroactive polymer, such as PEDOT (poly(3,4-ethylenedioxythiophene), poly(3,4-dioxypyrrole) (PXDOP), polyacetylene, polyaniline, polythiophene, poly(phenylvinylene) and derivatives thereof.

In a further version of the invention, the membrane or the material or polymer with an adjustable redox status is applied to a support structure formed of a nanoporous substance, whereby a particularly effective functionality can be achieved. The membrane or the material or polymer with an adjustable redox status is preferably located at least on an interior surface of the pores of the nanoporous substance or carrier structure. In this manner, the nanopores of the carrier structure can be advantageously used as the substructure for the pore structure. In this arrangement, the pore diameter is designed in dependence on the analyte to be detected and is adjusted to the above-mentioned diameter of the pores of the membrane.

The nanoporous substance preferably has a metal oxide, such as $Al_2O_3$, $In_2O_3$, MgO, ZnO, $CeO_2$ $Co_3O_4$, and/or the support structure for the controllable organic membrane or the polymer particularly preferably has at least $TiO_2$. However, any other suitable nanoporous substance could also be used. $TiO_2$ advantageously provides a support structure which is particularly lightweight, biocompatible and bioinert. In addition, the nanopore structure, composed of nanotubes, can be synthesized very easily and reproducibly. These highly uniform structures can be produced relatively easily by an anodization process. The pore size and layer thickness of this substrate can be easily adjusted during production on the basis of parameters. Generally, the layer thickness of several hundred micrometers is much larger than the diameter of the nanotubes.

Preferably, the entire sensor system is biodegradable, whereby it does not need to be removed from the body of the patient once it has ceased functioning, preventing undue strain on the patient. In addition, harmful substances, such as those that are present when a non-biocompatible and non-biodegradable sensor is used, are prevented from entering the body and posing a hazard to the health of the patient.

The sensor is advantageously formed to quantitatively determine the characteristic, whereby a determination of the concentration of the analyte, for example in bodily fluids, such as blood, urine, interstitial fluid or tears, can be easily determined. The quantitative determination can be carried out in a manner that minimizes components and structural space if the same region defines both a first (measuring) sensor and a second (reference) sensor. The measuring sensor and the reference sensor are formed integrally with one another, wherein in this context, "integral" is understood particularly to mean that measuring sensor and reference sensor are formed by the same component. The sensor reservoir is formed such that it serves in a first mode for reference measurement, and in a subsequent second mode for analyte measurement. Pore size is adjusted during reference measurement such that it is smaller than a diameter of the analyte, so that the analyte cannot penetrate into the sample volume. Molecules or structures that are smaller than the analyte, however, are able to penetrate into the sample volume. During analyte measurement, the pore size is then adjusted to the size of the analyte, thereby allowing the analyte to pass into the sample volume. The measurement signal for reference measurement is then subtracted as a background signal from the measurement signal for analyte measurement, whereby a final measurement value is obtained. In this manner, the background signal can be easily determined from interference effects.

In an alternative version of the sensor system, the sensor system has at least one second sensor which defines a reference sensor. Therefore, two different regions are provided as a first sensor and as a second sensor, whereby analyte and reference measurement can be carried out simultaneously or successively, resulting in a time savings. The first and second sensors, or the measuring sensor and the reference sensor, are preferably spatially separate from one another in the sensor system. The second (reference) sensor can be formed by any sensor deemed suitable by a person skilled in the art. Preferably, the second sensor is configured similarly to the first sensor, and has a reference reservoir which encloses a reference volume. The two sensors preferably differ from one another in terms of their pore size. The pore size of the organic membrane of the first sensor/measuring sensor allows the analyte to pass into the sample volume. The pore size of the organic membrane of the second sensor/reference sensor, adjusted to be smaller, prevents the analyte from passing into the reference volume. By correcting the measured signal of the measuring sensor by means of the reference signal, the final measured value is obtained. The two sensors preferably have switchable organic membranes, particularly electrically switchable membranes, which differ from one another in terms of the configuration of their switchable membranes and particularly in terms of the pore size adjusted thereto. The different porosities for the measuring and reference sensor are adjusted by using correspondingly different voltages, and/or by the duration of the voltage applied to the membranes belonging to the sensors.

This structure has the advantage that both the measuring sensor and the reference sensor contain the same detection system, and therefore drift and aging processes run similarly. Therefore, in a determination of the final measured value by the measuring sensor, the reference sensor, or both sensors, information regarding the drift (e.g., degrading of the detection system, change in temperature and other effects) of the sensor system can be advantageously collected. The subsequent measured values relating to drift can be corrected using a suitable correction term, or can be compensated for via a suitable method (electrical, mechanical or chemical/biochemical). If drift is so great that the mechanisms no longer are effective, then in an array system of similar sensor systems, a new sensor system can be activated.

During operation of the medical sensor system using the controllable organic membrane, the membrane is reversibly adjusted between an opened and a closed state of the reservoir. In this case, to detect the characteristic, in a first step the pore diameter of the controllable organic membrane is adjusted to a first diameter, and in a second step the pore diameter is adjusted to a second diameter, wherein the first diameter is smaller than the second diameter. The same steps can be utilized to detect the characteristic at a controllable organic membrane of a second sensor. In this manner, the measurement result of the measurement with analytes can be easily corrected by the measurement result of the background signal.

It is expected that molecules that interfere with and disrupt the detection system, such as other charge carriers, can also enter into the sensitive region of the sensor, or can become adsorbed to the "gate" of the FET. These can become adsorbed onto the sensitive sensor surface and form a non-specific charge transfer which affects a measurement signal. This can result in drift and disruption of the measurement signal, so that a suitable signal can no longer be derived. To minimize this, the sensor can incorporate at least one passivation layer which is applied to at least one region of the sensor, and is formed to saturate binding sites, particularly non-specific binding sites. This region is preferably the same region as the region that is coated with characteristic carrier receptor or with antigen binding partner, and particularly the "gate" of the FET. Alternatively or additionally, a surface which comes into direct contact with an implantation site and/or a bodily fluid, particularly an outer surface of an implant having the sensor system, can also be passivated against the adsorption of interfering factors from the body, particularly from the bodily fluid.

To achieve passivation, chemically inert and long-term stable substances can be used, particularly hydrophilic substances and/or polymers such as polyethylene glycol (PEG), PEG derivatives, hydrogels, dextran and/or any other substance deemed suitable by a person skilled in the art. This substance can adhere physically and/or bind covalently to the surface. In principle, binding could also be achieved by any other method deemed suitable by a person skilled in the art. The chain length and chain structure of the polymer are dependent on the nature of the characteristic carrier receptor that is used. Whether the characteristic carrier receptor is applied to the surface before or after application of the passivating layer or the passivating polymer to the surface is based upon the type of polymer that is used and the type of characteristic carrier receptor linker, or the binding sites thereof. For example, with PEG, it is possible to first bind the characteristic carrier receptor linker to the surface, to protect the binding sites thereof for the characteristic carrier receptor, and then to apply the PEG, and in a final step to bind the characteristic carrier receptor. It is preferred that the passivating layer is very thin so that the charge transfer can be measured with a high degree of sensitivity. Therefore, materials having low dielectric constants and thin layers within the nanometer range are preferred. One possibility for structuring thin layers for passivation and for suppressing undesirable measurement signals while simultaneously allowing anchor groups for linker molecules is offered by plasma polymers. These can be uniformly applied to the component, particularly one of the FET's, in a post-processing step.

To achieve these nanofilms, various monomers can be used. Proven versions of biocompatible nano-layers that repel proteins utilize simple hydrocarbons such as $CH_4$ or $C_2H_2$. These are preferably deposited in a high-frequency discharge by means of magnetron-based low-frequency discharge. The dielectric constants can be varied between 2 and 2.5 and the layer thickness can be varied between 10 nm and 70 nm, wherein a layer thickness of 20 nm is preferred. Linker molecules can also be coupled to these layers by means of benzophenone reactions. Fluorocarbons, such as $C_2F_4$ or $C_4F_8$ as monomers, can also be used for the hydrophobic coating, and can be polymerized in the gas discharge. In this case, the dielectric constant is higher, and can be adjusted between 3 and 3.5.

By means of the passivating layer, interferences with the surface of the FET—caused particularly by charged molecules—are suppressed. This advantageously leads to a low interference measuring signal. With the displacement principle, in the case of a large antagonist which is unable to escape from the sensor through the semipermeable membrane, and with the equilibrium mechanism between characteristic carrier receptor, analyte and antagonist, and the suitable passivating layer on the sensitive surface for a constant signal-to-noise ratio, the problem of the washing steps which are otherwise needed in immunological detection reactions can be avoided.

Sensors that are implanted in vivo typically have major problems with long-term stability, particularly when they come into contact with blood. Typically, once they have been implanted into the body, they exhibit a non-specific protein adsorption. These adsorbed proteins at least partially lose their tertiary or quaternary structure, and serve as anchor substrates for the attachment of cells. When triggered in this manner, an unspecified cell coverage and/or an extracellular matrix composed of protein fibers (e.g., collagen) form on the surface of the sensor or the implant, such as the semipermeable membrane, for example. This process is generally referred to as biofouling. In addition, a thrombus can form on the surface of the sensor or the implant.

These accretions further mean that a diffusion barrier to the analyte can develop that is not stable over time, and which directly influences the measurement signal. The cell coating or the extracellular matrix can result in both a drift and a delay of the measurement signal, so that the sensor can detect external changes in the characteristic or the analyte concentration only with a time delay. The diffusion barrier can become so large that the analyte can no longer reach the sensor, thereby preventing derivation of the signal.

To counter this, the sensor system can have at least one surface coating as an anti-fouling coating, particularly as an anti-biofouling coating, which is applied to at least one region of the sensor and is formed to prevent interactions with interfering substances. This region is preferably the organic semipermeable membrane, particularly the areas thereof that can come into contact with bodily fluid. Interfering substances in this case are constituents of structures, such as tissues and/or bodily fluids, which can come into contact with the sensor and/or the implant, and particularly cells and/or molecular constituents such as proteins, salts, ions and/or any other interfering substance deemed harmful by a person skilled in the art. The surface coating can have, for example, hydrophilic polymers or a hydrogel layer (PEG and PEG derivatives), which suppress an adherence of cells and molecules. By means of the surface coating as an anti-fouling coating, the sensor system can be advantageously formed to be resistant to interference in a structurally simple manner.

Additionally or alternatively, a sensor and/or implant surface can be modified in such a way that the reaction of the body is steered in a direction that is relevant to the stable functioning of the sensor over the long term. For example, one or more suitable coatings, suitable microstructuring, and/or suitable nanostructuring can be applied to or introduced into the sensor and/or the implant surface, wherein these features positively influence the integration behavior of the introduced implant and/or the reaction of the body to the implant, for example. For structuring on the surface, round, spherical, cylindrical, conical, square, rectangular, and elongated structures can be applied to or removed from the surface. These include grooves, tubes, solid cylinders, spheres, hemispheres, blocks and cubes.

In addition, structures from the bodily fluids, such as certain proteins or cells, for example, can be selectively attracted to the sensor and/or implant surface, immobilized, and the cells can be induced to proliferate, for example. In this manner, the integration and biofouling can be positively influenced, in order to form a diffusion barrier that will remain unchanged over time following an integration phase. In addition, a surface modified in this manner will not produce a thrombogenic effect, thereby limiting the risk to the health of the patient.

The sensor system preferably has at least one region having a surface whereupon specific recognition markers for cells are located, wherein the recognition markers are selected from the group consisting of peptides, proteins, antibodies, antigens, aptamers, molecularly imprinted polymers and polynucleotides having n≥1 monomer units (ribonucleic acid or RNA, deoxyribonucleic acid or DNA, peptide nucleic acid or PNA, locked nucleic acids or LNA). Here "molecularly imprinted" means the provision of a polymer skeleton with recognition domains. Molecular imprinting provides access to polymers that contain information. For example, polymers can be provided with the necessary selectivity through radical polymerization in the presence of a template (which in the most favorable case can later be removed through washing steps), in order to form affinities to similar structures. A method of this type is known from Vaidya et al., A. & L. Fischer, 2004: "Altering glucose oxidase to oxidase D galactose through crosslinking of imprinted protein" (ChemBioChem 5 (1): 132-135).

In this, the type of epitope determines the polymer selection. Acrylates and methacrylates are suitable as the skeleton. Azo-bis-(isobutyronitrile) (AIBN) is the preferred radical starter. The reaction can be run in solvents such as dioxan, $CHCl_3$ or THF, but also in other substances. With copolymers with acylacetate (hydrophilic groups can be well saponified to produce OH-groups), acylamine, acyl acids or styrene (interaction with aromatic epitopes), high binding affinities can be produced, in addition to high selectivity.

A "specific recognition marker" refers to a molecule which is embodied specifically for the adsorption of a certain cell type. In other words, a "recognition marker for cells" refers to a bond or a part of a bond which is specifically recognized by one, two or three cell types (preferably one) and can effect a binding of the cells of this type or these types to a surface on which the recognition marker is located. In contrast, cells of other types exhibit no such reaction. In the present case, the migration and proliferation of endothelial cells (EC) is preferably promoted.

A class of preferred cell types are those that recognize the recognition markers on the implant surface with the help of transmembrane proteins (integrins), chosen from the group of cells that carry integrins. Particularly preferred are cells belonging to the alfaVBeta3 ($\alpha v \beta_3$) subfamily. In addition to the above-mentioned endothelial cells, endothelial precursor cells also have the desired recognition sequences. (Blind et al.: "A novel Drug-Eluting Stent coated with an Integrin-Binding Cyclic Arg-Gly-Asp Peptide Inhibits Neointimal Hyperplasia by Recruiting Endothelial Progenitor Cells"; JA College of Cardiology; Vol. 47, No. 9, 2006; Garcia A. J.: Get a Grip, integrins in cell-biomaterial interactions"; Biomaterials 26; 7525-7529, 2005). The use of peptide sequences on stents is described in WO 2008/143933 A1. In this case, an accelerated healing by the formation of a cell sheet can also be achieved.

The sensor system with the sensor can be part of an implant. For the sake of simplicity, the following will refer to an implantable theranostic article or articles, which is to be understood as both a sensor or a sensor system alone and an implant with a sensor system and sensor.

Providing certain recognition markers on the surface of an implantable theranostic article, with the suitable selection of the markers on the basis (for example) of the location of insertion of the implantable theranostic article, causes the implanted article's surface to present a boundary surface to which the body will react with a defined, thin scarring and/or encapsulation, which will not continue to change after a certain period of time. It is particularly surprising that, after a relatively short growth phase, a tissue that in principle will not undergo further change is produced on the implanted theranostic article. As a result of this biomimetic surface, the article is then no longer identified by the body as a foreign object.

This aspect of the invention therefore represents a new approach. In the past, attempts were focused on creating bioinert surfaces and nanostructures for implant applications, which were encumbered by the disadvantage of thrombogenicity and a lack of specificity. In contrast, by using the specific recognition labels for cells, a (largely) constant and biomimetic surface is produced. In this case, the extent of cell coverage can also be controlled by the concentration of the specific recognition marker for cells on the surface of the implantable theranostic article. In principle, however, a relatively low cell coverage is produced, which will not further increase over time after a growth phase (or healing period). Therefore, this layer represents a surprisingly small diffusion barrier, wherein it is also surprising that a stationary state is also achieved with respect to a diffusion of analyte.

With a suitable binding method, it is possible for a person skilled in the art to control the actual integration process of the (desired) cell type. In this case, the formation of an endothelial cell layer is particularly preferred. In this arrangement, particularly when the membrane is being monitored, it is important that a diffusion of the analyte into the reservoir of the sensor system or the interior of the sensor can take place unimpeded. Typically, the molecules of greatest interest are small enough to ensure an effective diffusion through the endothelial cell layer into the interior of the sensor.

Article surfaces that are suitable for absorption are preferably chosen from the group consisting of titanium, medical stainless steel, such as preferably 316L, CoCr, magnesium and polymers. Polymers can be degradable under the conditions of use in the body, or can be permanent in the body. Groups that are suitable for forming covalent bonds on the surface of the implantable article include the hydroxyl group, the amino group, the carbonyl group and the mercapto group.

It is preferred for the recognition markers to be bonded to the implantable article via adsorption, covalent bonding or linkers. A bond linker within the context of the present invention is a molecule part that chemically ensures bonding between the specific recognition markers for cells and the surface of the implantable theranostic article. The bond linker is composed of an anchor group and a spacer group. The spacer group has a chain length of 1-30, preferably 5-12 atoms. Preferred suitable anchor groups are: acyl acid, phosphonates, thiols, isocyanates and particularly preferably isothiocyanates. The following are preferably used as spacers: PEG, polyproline, adipic acid, preferably aminohexanoic acid. Additional reagents for coupling, such as N,N'-carbonyldiimidazole (CDI), 1-(3-dimethylaminopropyl)-3-ethylcarbodiimide (EDC) or disulfosuccinimidyl-tartrate (DST) are also preferred under certain application conditions.

It is preferred for the specific recognition marker to be an oligopeptide. Oligopeptides include up to ten amino acids and can be used with particularly positive results as recognition markers for certain types of cells, due to their size and on the basis of their functioning. A particularly preferred involves an implantable article wherein the molecular recognition marker includes or consists of an RGD or cRGD sequence.

Particularly preferred is a specific recognition marker for cells selected from the group consisting of compounds of formula I:

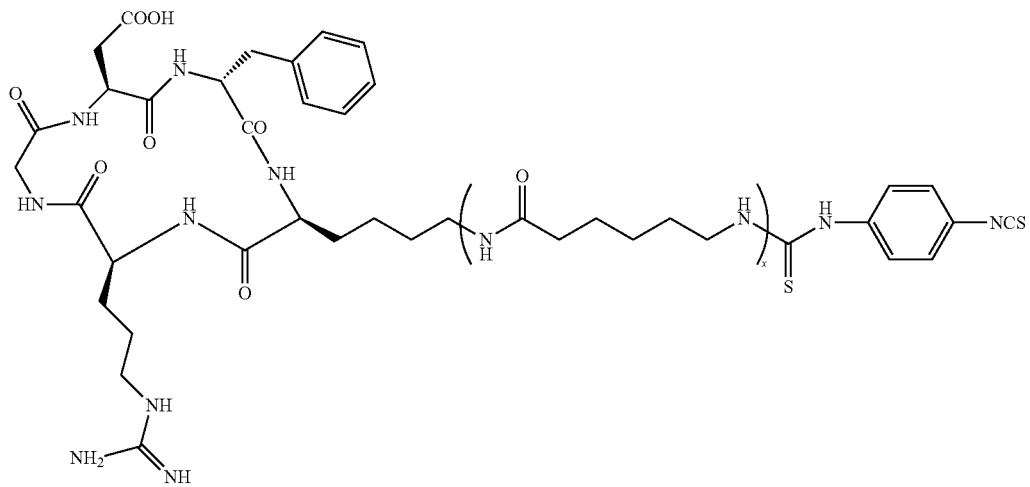

Formula I $x = 0, 1, 2, 3, 4, 5$ or $6$ and
compounds of formula II:

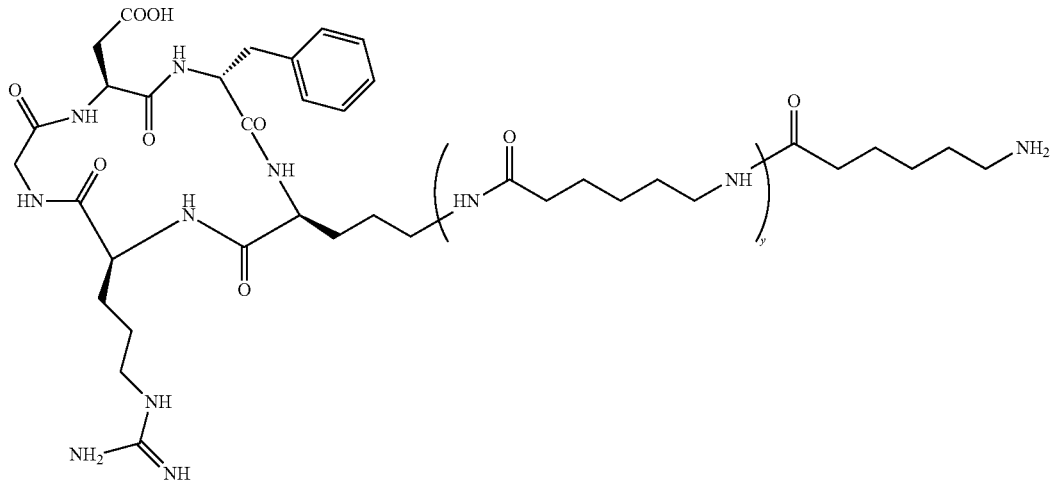

Formula II $y = 0, 1, 2, 3, 4$ or $5$.

It is further preferable for the surface of the article, or parts of the surface, to have a metallic, ceramic or polymeric character. Moreover, the surface of the implant (or parts of the surface) can have hydrophobic or hydrophilic properties, depending upon the intended use, and can have a cationic or anionic or metallic character.

The surface of the implantable theranostic article can also undergo further modifications which bind or repel special constituents of the bodily fluid. As such modifications, inorganic or organic molecules, such as polymers, peptides, proteins, aptamers, molecularly imprinted polymers RNA, DNA, PNA, LNA, siRNA and nanoparticles, can be linked to the article surface via physical absorption or covalent bonding. A partially or fully bioresorbable or biodegradable surface is also conceivable.

The invention further involves a medical sensor array having at least two sensor systems. These can be the same sensor systems which detect or determine the concentration of the same analyte in temporal succession. The sensor systems can also be used simultaneously for analyte measurement and for reference measurement. A limited lifespan of a sensor system can be advantageously extended to a good overall lifespan by using an array of multiple sensor systems. Alternatively, an array of sensor systems is also possible which are capable of detecting different analytes and/or the concentrations thereof, simultaneously or in temporal succession. Where multiple sensors are used, several specific antibody-antigen-antagonist trios can be developed.

The invention further involves a medical implant having at least one medical sensor system, and/or having a medical sensor array. In this context, an "implant" is understood particularly as a body which performs at least one replacement function, permanently or for an extended period of time, when implanted into an human and/or animal body. In this case, any medical implant deemed suitable by a person skilled in the art could be used, for example, an implant for recording physiological parameters, a cardiac pacemaker, a defibrillator, a cardioverter, a cerebral pacemaker, a neural stimulator, a renal pacemaker, a duodenal pacemaker, a cardiac implant, artificial heart valves, a cochlear implant, a retinal implant, a dental implant, an implant for joint replacement, a vascular prosthesis, or particularly advantageously a stent, such as a coronary stent, a renal artery stent, or a urethral stent, and a drug delivery system. With an implant of this type, diseases such as cardiac insufficiency, high blood pressure, renal insufficiency and/or Diabetes mellitus—which are frequent, chronic diseases that require intensive treatment and are therefore costly—can be better monitored and treated. The described modification of the surface of the membrane, for example, is particularly well suited for an implant, because many implant surfaces regularly come into contact with bodily fluid, particularly blood, wherein a defined integration is of particular importance.

In this context it is particularly surprising that a sensor for an implantable theranostic article, having a surface covered by specific recognition markers for cells, can be achieved wherein the resulting cell layer is sufficiently permeable to the respective analyte. This applies even where the part of the surface of the implantable sensor that is formed by a semipermeable membrane (permeable to the desired analyte) also includes specific recognition markers for cells on its (outer) surface.

Moreover, the sensor or the in vivo measuring device can contain a telemetry unit, by means of which the measured values can be transmitted to an external device for evaluation and/or display. The telemetry unit can be embodied as unidirectional, or bidirectional such that the implanted sensor or measuring device can be controlled via an external device. A drug can be administered manually to the patient in accordance with the output of the measurement signal. It is further possible for the implant or the article to contain an active ingredient dosing system, e.g., an implantable article which is capable of administering a drug in a controlled fashion over an extended period of time. An active ingredient dosing system of this type can be a "closed loop" system, i.e., an automatic drug dosing system can be controlled on the basis of the determined analyte concentration and triggered by the sensor, and a drug can be administered in order to counteract critical events. It is further possible for data to be transmitted from the external device to the active ingredient dosing system, wherein the transmitted data functions as a trigger for administration of the substance. This transmission of data can be automatic. Alternatively, it is possible for a trigger for the active ingredient dosing system to be issued manually. With the version according to the invention, critical physiological values can be detected early, evaluated, corrected if necessary, or the occurrence thereof prevented.

The sensor or the in vivo measuring device can also be a partial component of a body-area network and/or a telemonitoring system, i.e., additional sensors, also connected to one another via wireless telemetry and/or communicating with an eternal device, can detect in parallel physiologically relevant parameters such as pressure, pulse, EKG, EEG, biochemical variables, and/or other parameters deemed suitable by a person skilled in the art. The implantable, miniaturizable sensor can be controllable, for example, via a chip in a cardiac pacemaker capsule and via an electrode cable. The power supply (e.g., battery, fuel cell) supplies the necessary power for the functioning of the sensor and for data transmission. An alternative power supply for an implant consists in providing an external power source and transferring the power required for operating the implant by means of inductive coupling with the implant.

The invention further relates to a method for operating a medical sensor system for detecting at least one characteristic of an human and/or animal body including at least one sensor, a first characteristic carrier and a characteristic carrier receptor, wherein the first characteristic carrier differs in at least one characteristic parameter from a second characteristic carrier that is present at least at the time of detection.

It is proposed that the at least one sensor, in the detection of the at least one characteristic, is located in vivo and the sensor detects a characteristic change caused by a reversible displacement of the second characteristic carrier from the characteristic carrier receptor by the first characteristic carrier. In particular, a change in charge or a reduction of the bonded charge to the sensor or to the "gate" of the FET is measured and evaluated. This is accomplished by the displacement of the highly charged antagonist from the antigen binding partner by the analyte, which carries only a low charge. With this measuring principle, a method is provided, which is capable of functioning reliably over a period of months and years in vivo. In addition, it reacts sensitively and rapidly to changes in the conditions within the measuring substance.

BRIEF DESCRIPTION OF THE DRAWINGS

Exemplary versions of the invention are discussed in greater detail below with reference to the accompanying drawings, which show.

DETAILED DESCRIPTION OF EXEMPLARY VERSIONS OF THE INVENTION

Figure 1:
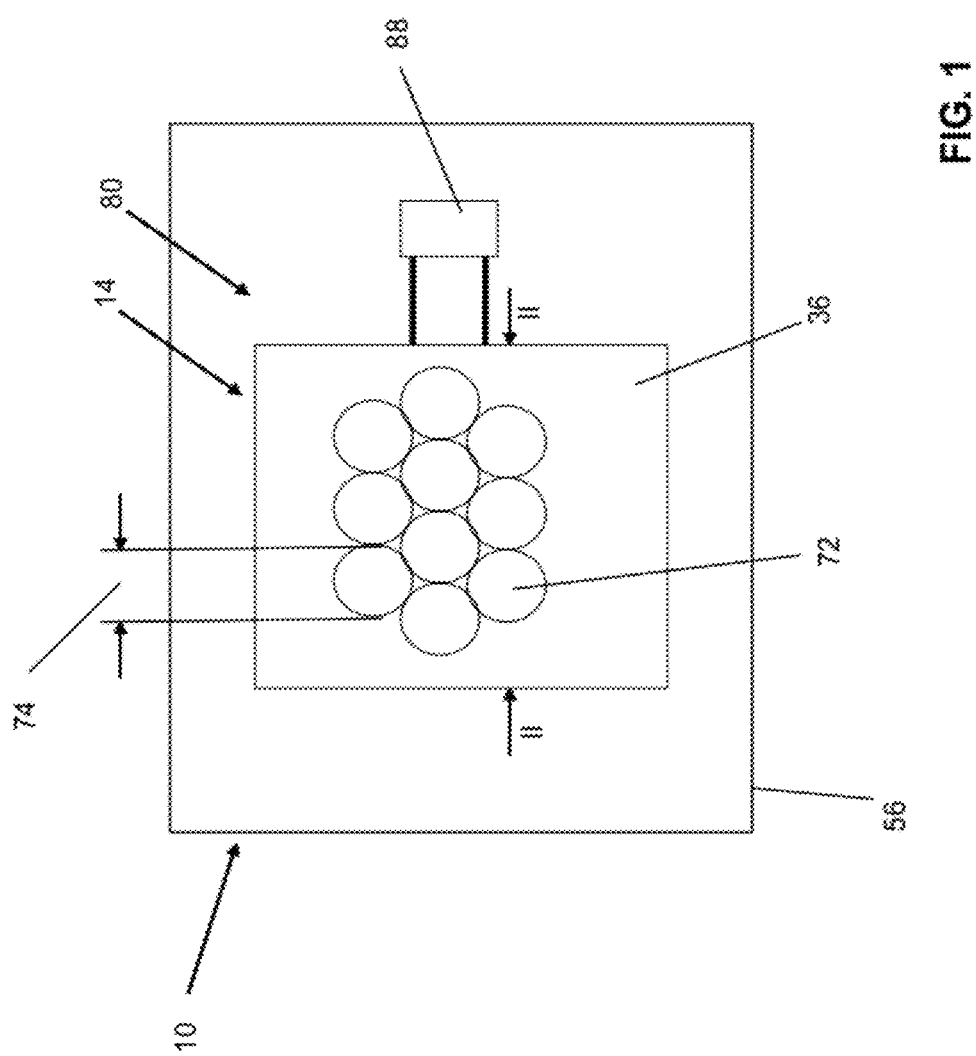
FIG. 1 a schematic plan view of a sensor system according to the invention.

In the drawings, functionally similar or equivalent elements are identified using the same reference signs. The drawings are schematic illustrations of the invention, and they do not depict specific parameters of the invention. The drawings further depict merely typical versions of the invention, and are not intended to restrict the invention to the illustrated versions. In the interest of avoiding unnecessary repetition, where elements in a drawing are not specified in detail, reference is made to the respective description of the elements in preceding drawings.

Figure 5:
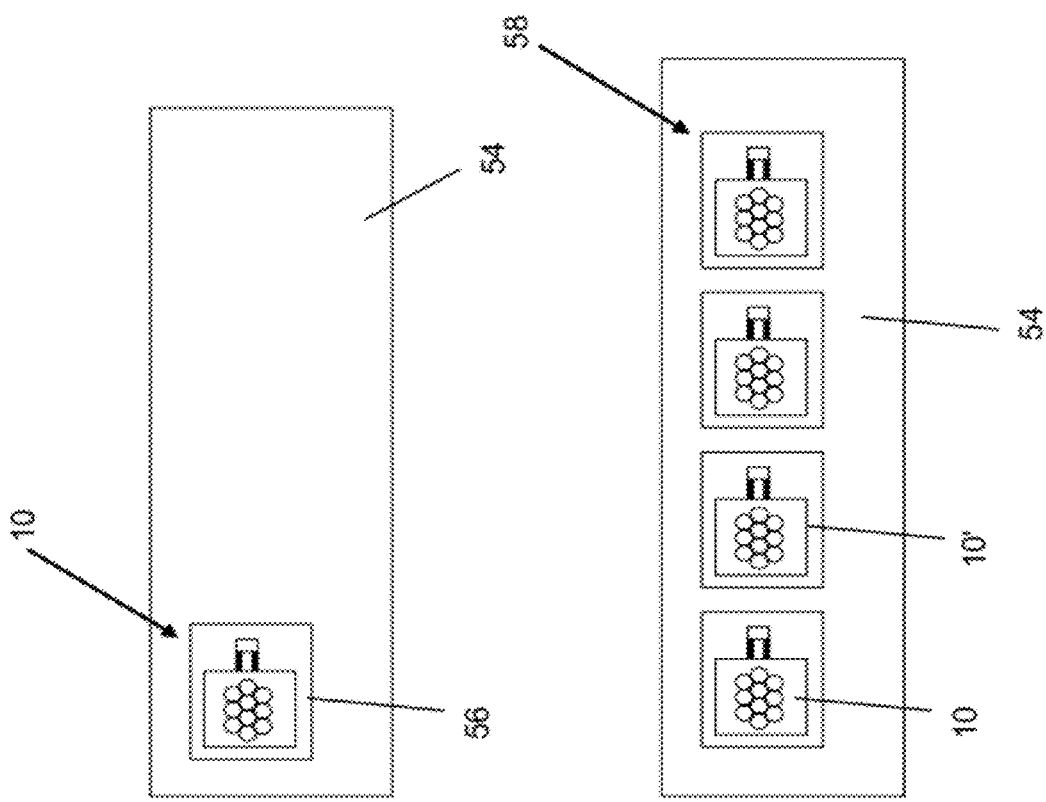

FIG. 1 shows a schematic plan view of a medical sensor system 10 having a sensor 14, arranged in a housing 56, for detecting a characteristic 12 in a human body (not shown here). Several sensor systems 10, 10' can be combined in a single medical sensor array 58, as shown in FIG. 5B. In this case, after a first sensor system 10 has been used, or once the first sensor system 10 has reached the end of its lifespan, a second sensor system 10' can be activated. In this regard, the sensor system 10 (FIG. 5A) or the sensor array 58 (FIG. 5B) can be implanted into the human body, as by attaching it via an anchoring device (not shown in detail here) to a medical implant 54. The implant 54 could here be a memory shape structure, for example, such as a stent or a meandering structure, for implantation in an artery or vein (not shown). The anchoring device can be permanent or removable. In this manner, the sensor 14 is located in vivo for detection of the characteristic.

Figure 2:
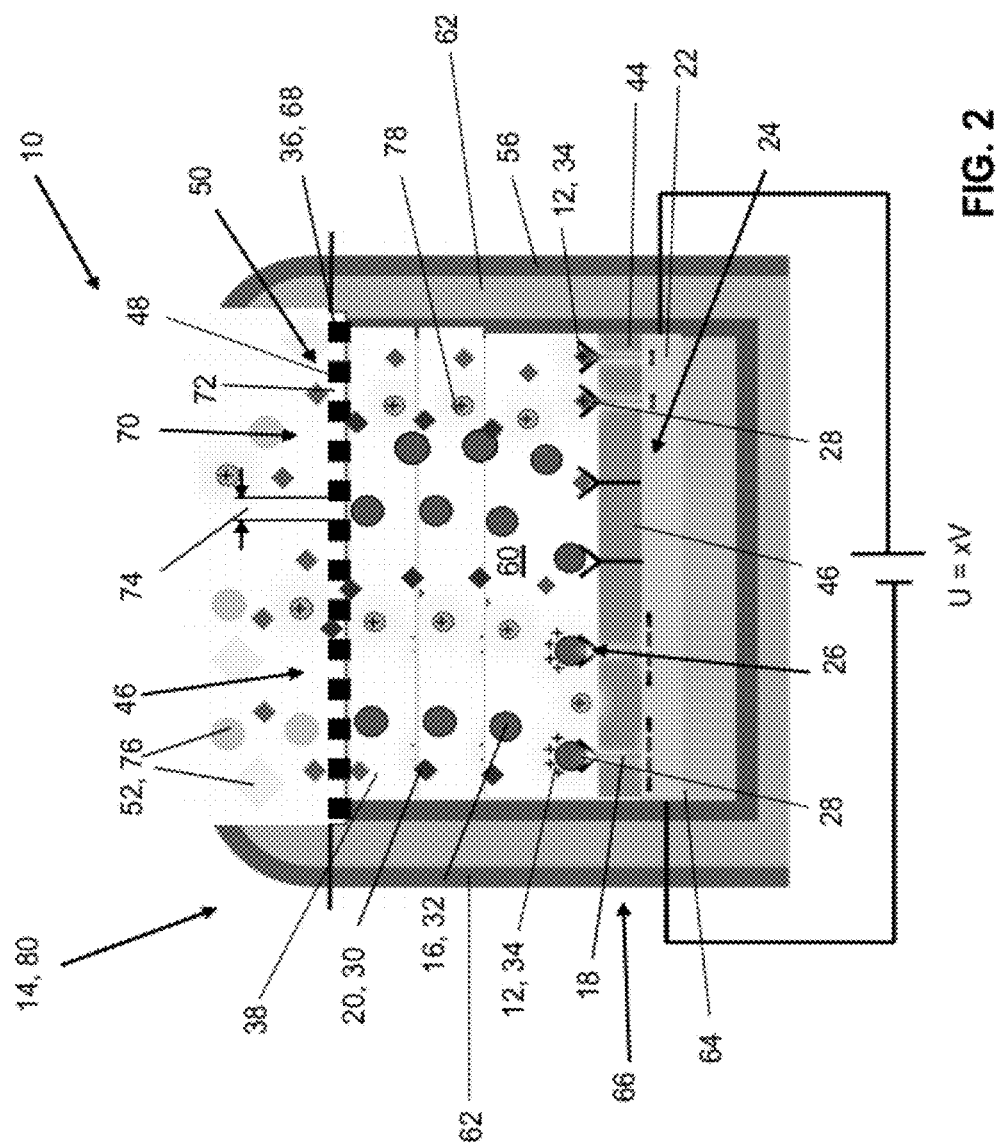
FIG. 2 a schematic cross-sectional illustration along the line II-II of the sensor system of FIG. 1, including a detection system, FIG. 3 a schematic cross-sectional illustration of the sensor system of FIG. 1 including a measuring sensor and a reference sensor, with pores of different sizes, FIG. 4 the sensor system of FIG. 1 with additional components, FIG. 5A an implant equipped with a sensor system according to FIG. 1, FIG. 5B an alternative implant equipped with a sensor array having four sensor systems according to FIG. 1, FIG. 6 a schematic illustration of a molecular imprinting of polymers, FIG. 7A a schematic cross-sectional illustration, similar to line II-II of FIG. 1, of an alternative sensor system having a controllable membrane with closed pores, FIG. 7B the sensor system of FIG. 7A with the pores in an opened state for a reference measurement, FIG. 7C the sensor system of FIG. 7A with the pores in an opened state for an analyte measurement, FIG. 8A a detailed illustration of a pore of FIG. 6A in the closed state, and FIG. 8B a detailed illustration of a pore of FIG. 6C in the opened state.

As seen in FIG. 2, which illustrates a cross-section along the line II-II in FIG. 1, the sensor 14 has a sensor reservoir 38, which encloses a sample volume 60 within four sides 62 and a base 64, wherein only two sides 62 are visible here. A detection system 66 is provided in the reservoir 38 and/or on the base 64. In addition, the sensor 14 has a selection structure 68 located on a sixth side 70 of the reservoir 38 opposite the base 64, or which forms the sixth side 70 of the reservoir 38. The selection structure 68 is defined by an organic semipermeable membrane 36, by means of which the reservoir 38 can be closed off.

The sensor system 10 or the detection system 66 has several characteristic carrier receptors 18, coated to define a receptor layer on a region 24 of the sensor 14 or of the base 64, in a density suitable to a person skilled in the art. The base 64 has a semiconductor component 22 in the form of an extended-gate Field Effect Transistor (seFET), and the region 24 forms a "gate" of the seFET. Each characteristic carrier receptor 18 is formed by a molecule having an antigen recognition site 26, and may be a Fab fragment of a monoclonal antibody against a protein or other analyte 30 to be detected (with this analyte 30 containing the antigen 28). The characteristic carrier receptor 18 has also been modified by means of a molecular biological process so that the affinity for the antigen has been decreased at the antigen recognition site 26, whereby the binding is reversible (not shown in detail). For example, a binding constant of the antigen-antigen recognition site 26, 28 may be approximately $1 \times 10^{-8}$ mol/l.

The analyte 30, in this case cystatin C, also represents a second characteristic carrier 20. The antigen 28 is further presented by an antagonist 32 of the analyte 30 that is present in the sensor 14 or in the sample volume 60 thereof. This antagonist 32 is an artificial and recombinant protein developed through epitope mapping, which carries a poly-L-lysine modification. It further represents a first characteristic carrier 16 as a constituent of the sensor 14. Furthermore, the antagonist 32 and the characteristic carrier receptor 18 have been modified via molecular biological methods such that a number of amino acids contained in the sequences thereof, and irrelevant to the binding of the respective opponent, but which are recognized by metabolic enzymes as a degradation starting point (e.g., serine of serine proteases), are replaced by other amino acids that will not modify the protein structure. Thus the molecules will protect against enzymatic degradation in the body, thereby increasing long-term stability (not shown in detail).

The organic membrane 36 is formed in such a way that the first characteristic carrier 16 or the antagonist 32 is retained at all times in the reservoir 38, and such that the second characteristic carrier 20 or the analyte 30 is able to pass through the membrane 36. For this purpose, the organic membrane 36 made of a polymer has multiple pores 72, which are arranged distributed homogeneously over the surface. In FIG. 1, for the sake of clarity, only a few pores 72 are shown. (In addition, the pores in all drawings are shown enlarged rather than true to scale). To permit diffusion of an analyte 30 in the form of cystatin C (which is preferred), the diameter 74 of the pores 72 of the organic membrane 36 must be greater than about 5 nm. However, it must be smaller than 20 nm so that the antagonist 32 will be retained in the reservoir 38. If the analyte 30 were glucose, for example, a pore diameter of approximately 1 nm would be sufficient for the glucose to pass through the membrane. Additional cells or molecules 76, which are larger than the pore diameter 74, are retained by the membrane 36. However, smaller molecules 78 are able to pass through the membrane 36. The membrane 36 and the semiconductor component 22 are connected to the housing 56 in such a way that an exchange of substance is possible only via the pores 72 of the membrane 36 and not via a connection site between the membrane 36 and the housing 56.

The first and second characteristic carriers 16, 20 both have the characteristic 12 that is to be detected. In this case, the characteristic 12 represents a charge 34 of the first characteristic carrier 16 or of the antagonist 32, and also of the second characteristic carrier 20 or of the analyte 30. As a result of the poly-L-lysine modification, the first characteristic carrier 16 has a higher positive charge 34 which is higher than that of the second characteristic carrier 20. The first characteristic carrier 16 therefore differs from the second characteristic carrier 20 in terms of a characteristic parameter, namely charge intensity.

The sensor 14 utilizes a label-free immunological detection method in which the analyte 30 can be measured reversibly and on the basis of its concentration. The "gate" of the seFET has the bound characteristic carrier receptors 18 that selectively recognize the analyte 30. In the absence of the analyte 30, and particularly before the first measurement of antagonist 32 present in the sample volume 60, these are saturated (see FIG. 3 at right). The high charge 34 of the antagonist 32 generates a measurable charge transfer on the sensitive surface of the semiconductor component 22, thereby generating a measurement signal on the seFET. By saturating the sensor 14 with the antagonist 32, the measurement signal in the absence of the analyte 30 is 100%.

If the analyte 30 then escapes from the measurement substance (e.g., blood) which encloses the sensor 14, and enters the sample volume 60 of the sensor 14 via the semipermeable membrane 36, the analyte 30 can disrupt the bond that is present between the antagonist 32 and characteristic carrier receptor 18. If the analyte 30 is then present on the active surface, due to their similar antigen 28, the analyte 30 and antagonist 32 compete equally in a balanced manner for the antigen recognition site 26 of the antibody fragment. Therefore, the antigen 28 of the analyte 30 results in a reversible displacement of a number of the antagonists 32 that carry a high charge 34 and are bound to the characteristic carrier receptor 18. A concentration-dependent equilibrium between bound analyte 30 and bound antagonist 32 is established, wherein the charge transfer is different for analyte 30 and antagonist 32. In general, the more analyte 30 that is bound, the lower the measurement signal that can be derived.

The sensor 14 determines electrical status variables and/or a change in voltage. Due to the large difference in charge between analyte 30 and antagonist 32, the change in concentration is clearly detectable. In this case, the analyte concentration is proportional to the measured signal. In other words, during the detection process, the sensor 14 determines a change in characteristic (e.g., change in charge) which is caused by the reversible displacement of the first characteristic carrier 16 from the characteristic carrier receptor 18 by the second characteristic carrier 20. If the concentration of analyte 30 in the blood (and therefore also in the interior of the sensor 14) decreases, antagonists 32 again bind predominantly to the characteristic carrier receptor 18 and the measurement signal at the seFET 22 again increases. It is also clear from FIG. 2 that analytes 30 and antagonists 32 that have not bonded precisely to the antigen recognition site 26 do not contribute to generating the measurement signal.

The receptor layer that is applied to the gate 24 of the seFET 22 does not occupy all binding valencies of the surface of the gate 24. Additional free or unsaturated binding sites 46 of the region 24 of the seFET 22 that are still present must be saturated, so that interferences by other charged molecules, such as miniature molecules 78, can be effectively prevented. Therefore, a passivating layer 44 is applied to the region 24 of the seFET, which layer is embodied to saturate non-specific binding sites 46. The passivating layer 44 is formed by a polymer, such as polyethylene glycol (PEG), for example.

In addition, the sensor system 10 has a surface coating 48 applied to a region 50 of the sensor 14 so as to prevent interactions with interfering substances 52, such as cells and constituents or molecules 76 of the measuring substance (e.g., blood). The region 50 is formed by a surface of the membrane 36 which can come into contact with the measuring substance. In principle, other regions of the sensor system can also be coated.

Figure 3:
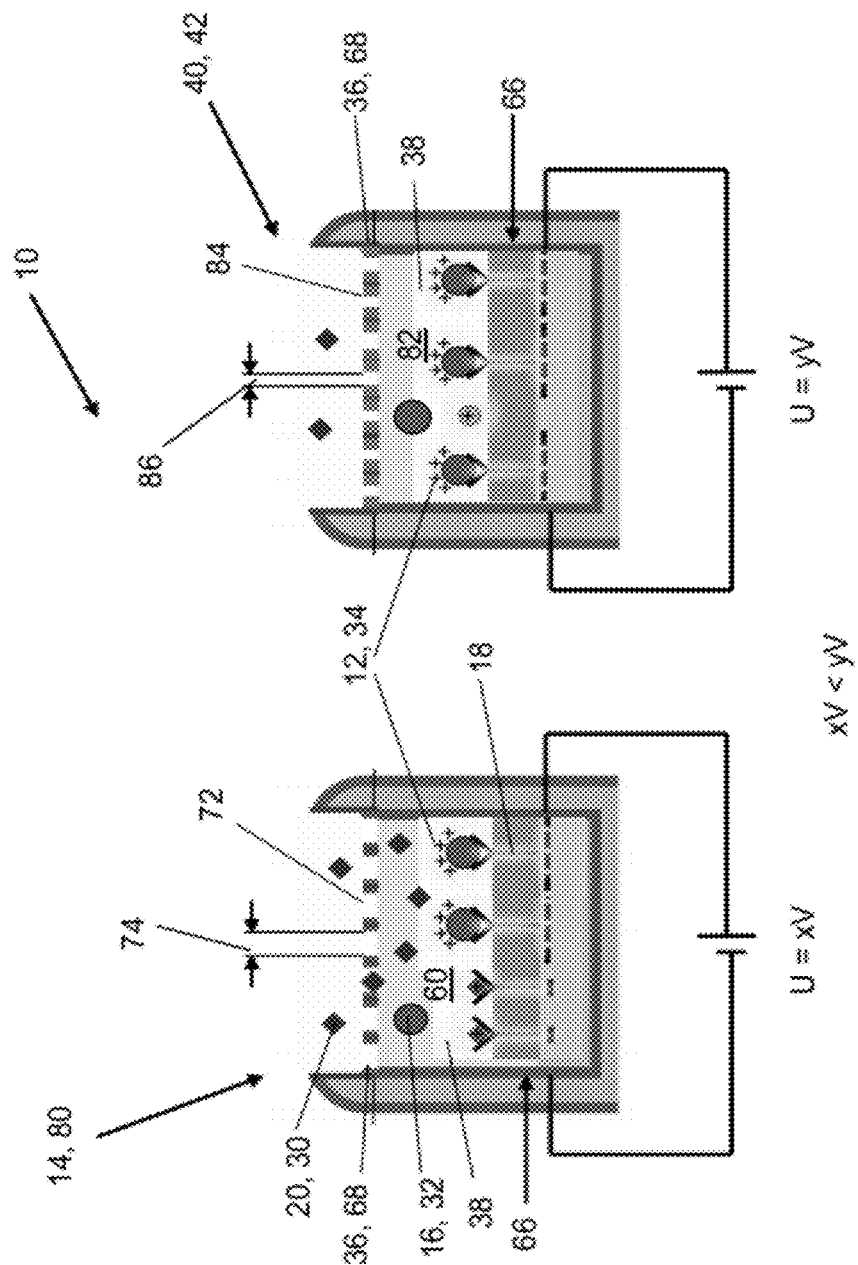

As is shown in FIG. 3, in addition to the sensor 14 (which defines a measuring sensor 80), the sensor system 10 also has a second sensor 40 which defines a reference sensor 42. The reference sensor 42 carries out a reference measurement which seeks to detect as many interference signals as possible. These sensors 14, 40 are spatially separated from one another in the same housing 56. Further, each sensor 14, 40 has a reservoir 38 which encloses a sample volume 60 or a reference volume 82. Each reservoir 38 is equipped with a semipermeable organic membrane 36. The membrane 36 of the reference sensor 42 has pores 84, the diameters 86 of which are smaller than the diameters 74 of the pores 72 of the membrane 36 of the measuring sensor 80. The pore diameters 86 of the membrane 36 of the reference sensor 42 are adjusted precisely such that the analyte 30 is unable to penetrate into the reference volume 82, and amounts to about 5 nm, for example. However, all smaller molecules 78, which could impair an assay of the analyte 30, are able to pass through. The reference measurement therefore determines the 100% signal at the point of saturation of the characteristic carrier receptors 18 with the antagonists 32, and the signals of the remaining charged substances or miniature molecules 78 that interact with the gate of the seFET. As was described above, the pores 72 of the membrane 36 of the measuring sensor 80 are dimensioned as about 10 nm, such that the analyte 30 (e.g., cystatin C) is able diffuse into the sample volume 60 to be measured. To obtain a final measurement result for the concentration of analyte 30, the measurement result of the analyte measurement is then corrected by the measurement result of the reference measurement.

Alternatively, sensor system 10 may also function without a reference sensor by generating a reference signal in the absence of the analyte or at low concentrations. For example, when the patient is healthy, a reference signal may be generated in the sensor 14 itself. In this manner, a reference point can be determined, by means of which sensor drift or gradual sensor degradation (by autolysis of the molecules, degradation of the measuring sensor layer in the seFET, or influences of the body on the implant) can be removed by calculation.

Figure 4:
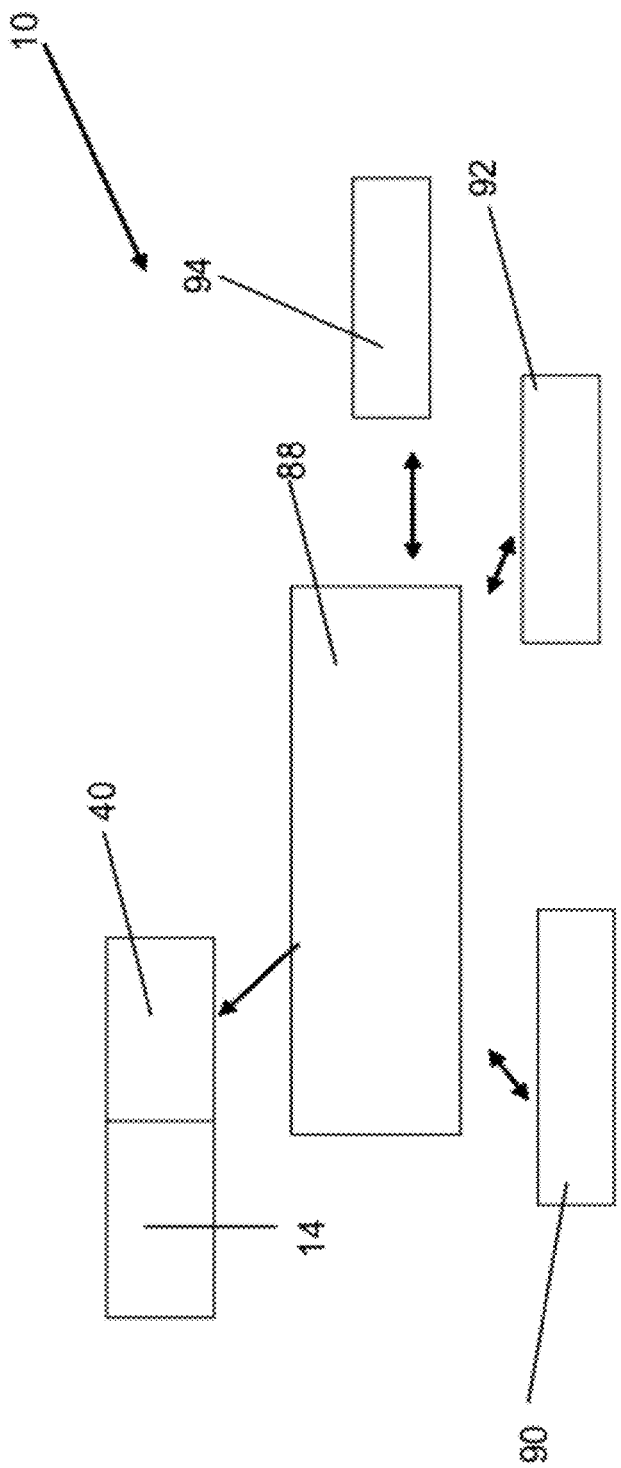

In FIG. 4, the constituents of the sensor system 10 are illustrated schematically. In addition to the sensors 14, 40, the sensor system 10 has a control device 88 having, for example, conductor tracks and/or additional electronic components (not shown here), a program memory 90, a telemetry unit 92, and a power source 94. By means of the telemetry unit 92, the values detected by the sensor system 10 can be transmitted to an external device (not shown). The telemetry unit 92 is preferably configured for bidirectional communication so that the sensor system 10 can be controlled by means of an external device. In addition, the sensor system 10 can communicate by means of the telemetry unit 92 with additional implanted devices, in order to control, for example, a treatment or dosing of drug by these additional implanted devices on the basis of the measured sensor values.

Alternatively or additionally, a region of the sensor system 10 and/or of the implant 54 can have a coating or a recognition coating 96, which has molecular recognition markers for cells, wherein the recognition markers are peptides or oligopeptides. Once the sensor system 10 has been implanted into the bloodstream, endothelial progenitor cells from the bloodstream and endothelial cells are attracted by the special coating 96, and settle on the surface of the article, proliferate and, after several days, form a monolayer of endothelium. The endothelial cells may also grow over the semipermeable sensor window 36, but intermediate cell pores 72 are large enough to allow the analyte 30 or the cystatin C to diffuse out of the adjacent bodily fluid into the sample volume 60 (not shown). Three examples of the production of the recognition coating 96 are described below.

Example 1 of the Surface Coating

A sensor head which has been cleaned in oxygen plasma or by rinsing with the sequence of solvents dichloromethane, acetone, methanol and millipore water, is further treated as follows. A 1 mM solution of hydroxyundecyl phosphonic acid in dry tetrahydrofuran (THF) is produced. The sensor head is suspended in this, and the solvent is removed by evaporation over a period of one hour, wherein the meniscus of the solution migrates over the surface of the sensor. The sensor head is then tempered for 18 hours at 120° C. and then rinsed with THF solvent. The surface pretreated in this manner is placed in a 0.3 M solution of carbonyldiimidazole (CDI) in dry dioxan for 15 hours. The substrate is then rinsed two times for 10 minutes each with dry dioxan and then dried in a nitrogen stream. A solution of the compounds to be coupled (in this case a cyclic pentapeptide according to formula II in which y=2 (approx. 50 µg/ml) in PBS buffer (amino acid-free)) is then applied to the surface treated in this manner and agitated overnight at 4° C. The sensor head is then rinsed with buffer.

Example 2 of the Surface Coating

A sensor housing made of titanium (Ti), cleaned according to Example 1, which consists of a cylinder having a diameter of 3-7 French, which at one head end has a passage for a sensor cable and at the other end has a sensor window consisting of a semipermeable membrane, is further treated as follows. A 3 mM solution of 3-(4-oxybenzophenone) propylphosphonic acid in dry tetrahydrofuran is produced. The cleaned surface is sprayed three times with this solution. The housing is then tempered for 12 hours at 120° C. and then rinsed with the solvent THF. The titanium housing is placed in a solution of the compounds to be coupled (in this case a cyclic pentapeptide according to formula II in which y=2 (about 500 µg/ml) in PBS buffer according to Example 1 and agitated overnight at 4° C. The next day, the Ti sensor surfaces are removed from the solvent, dried, and exposed at 260 nm to 100 mW/cm$^2$. Non-bonded protein is washed off.

Example 3 of the Surface Coating

The cleaned sensor housing made of titanium (see Example 2) are placed in a mixture of toluene, triethylamine and 3-aminopropyltriethoxysilan and incubated for 14 hours at room temperature. After the reaction has run, the sensor is washed in toluene and tempered for 1 hour at 135° C.

Composition of the silanization solution: 10 ml toluene, dried; 0.5 ml Triethylamine; 1 ml silane 3 aminopropyltriethoxysilane.

The cleaning step (rinsing the Ti substrate with trichloromethane) is followed by activation with 1,1'-carbonyl diimidazole (CDI). The silanized and rinsed Ti substrates are placed in CDI for 5 hours. For this purpose, the CDI is dissolved in dry dioxan. Suitable for this is a parent solution of 2.5 g/50 ml CDI in dioxan, which can be kept for several days (2 days dry). The substrates can be easily moved at room temperature. Following activation, the substrates are removed and rinsed with dry dioxan. For coupling the cyclic peptides according to formula I in which x=2, the activated Ti substrates are dipped in the peptide solution in a concentration of 5 mg/ml, and coupled at 4° C. overnight (min. 12 hours). The reaction is appropriately run in 125 mM sodium borate with 0.066% SDS at a pH level of 10.0. The solution can be reused afterward, or multiple surfaces can be treated with this solution.

Following coupling, the sensors 14 are washed three times with 5 ml of the borax buffer (above), then another three times with water. The peptides that can still be analyzed following these washing steps are bonded covalently.

The implantable sensors 14 coated in Examples 1 to 3, following implantation and an integration phase, all demonstrated a definite, single-layer scarring which exhibited no change over time and is non-thrombogenic. The sensors 14 were all ready for use for at least 6 months. The semipermeable membranes 36 of the sensors 14 remained permeable to the analyte 30 in a constant manner, so that reliable and reproducible signals were generated. Therefore, implantable implants 54 according to the invention generally have a functionality of at least three months following implantation, preferably at least six months, and particularly preferably at least one year.

Figure 6:
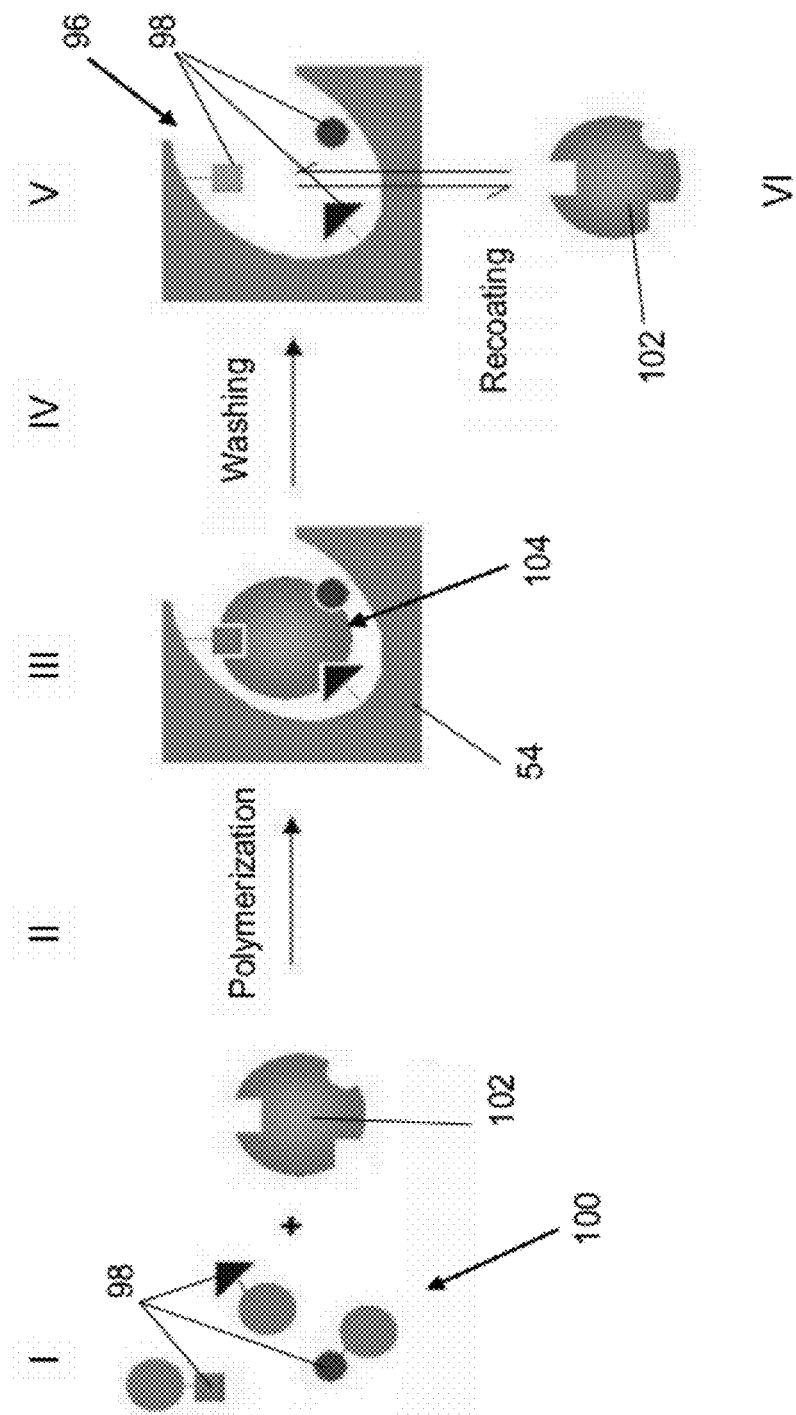

FIG. 6 shows a further option for modification of the implant surface by imprinting specific recognition markers, for example, polymers 98. In this case, a polymer mixture 100 is mixed with a template 102 (I) and is polymerized (II). The resulting complex 104 is applied to the implant 54 for the coating thereof (III). The implant 54 is then washed (IV), wherein polymers 98 of the polymer mixture 100 remain on the implant 54 as a recognition is coating 96 (V) and the template 102 is washed with polymer mixture 100 for recoating (VI). In this manner, a "self-healing" surface with good biocompatibility can be produced. With the long-term stable templates 102, structurally adapted to the surface of the implants, special polymers 98 can be bound selectively and stably to the surface in vivo, specifically via molecular recognition events. Good biocompatibility can thereby be achieved. Other polymers which are structurally different from 98, and which could, for example, trigger the coagulation sequence as a result of adhesion to unmodified surfaces, cannot bind to the templates 102, or can bind thereto only briefly, due to the deviating structure, and are rapidly displaced by the actual polymer 98 from the templates 102. If the polymer 98 in the template 102 loses its three-dimensional structure due to chemical modifications/degradations, it will desorb from the implant surface, thereby creating space for polymers 98 having the correct structure. The biocompatible surface renews itself.

In FIGS. 7A-C, 8A and 8B, an alternative version of the sensor system 10 are illustrated. Components, features and functions that remain unchanged are identified by the same reference numbers as in prior drawings. However, to differentiate this version from the prior version, the letter "a" is added to the reference signs of the modified version of FIGS. 7A-C, 8A and 8B. The following description primarily limited to the differences from the version in FIGS. 1 to 6, and the reader is directed to the foregoing description of the version of FIGS. 1 to 6 with respect to components, features and functions that remain the same.

In FIGS. 7A to 7C, cross-sectional illustrations of an alternative medical sensor system 10 are shown in three different states (closed state, reference measurement state, and analyte measurement state). The detection system 66 is not shown in detail. The states can be adjusted via an electrically controllable organic membrane 36a which is connected via a carrier structure 106 to the housing 56. The carrier structure 106 is formed by a nanoporous substrate made of $TiO_2$ and therefore has a high biocompatibility. The carrier structure 106 to is formed by nanotubes 108 which extend perpendicular to the base 64 of the reservoir 38 and parallel to one another. Each nanotube 108 has a nanopore 110 that is permeable to the analyte 30. The size of the nanopore 110 is designed in accordance with the analyte to be detected; to illustrate, for measuring cystatin C, a diameter of about 10 nm is preferred, whereas for measuring glucose, a diameter of about 1 nm is preferred. The interior surface of the nanopore 110 is coated on a side that faces the base 64 with a conductive material, e.g., gold, by a sputtering process. The controllable organic membrane 36a is located on the surface that faces the sample volume 60. The controllable organic membrane 36a is electropolymerized from a solution of the components thereof on the gold surface of the nanopores 110. In addition, the controllable organic membrane 36a is formed by an electroactive material or polymer 112, e.g., material containing polypyrrole (PPy) 114 and dodecyl benzene sulfonate (DBS) 116 (see FIG. 8). To control the controllable organic membrane 36a, conductor tracks, not shown in detail here, are applied to the carrier structure 106 at the level of the gold coating, and are connected to a control device 88 integrated into the sensor 14, whereby the controllable organic membrane 36a can be electrically controlled.

When producing the carrier structure 106 or the nanotubes 108, the pore diameter can be adjusted to the analyte 30 to be used, and different carrier structures can be provided to form the skeletons for different controllable organic membranes 36a. The layer thickness of the membrane 36a is much greater (for example, several 100 μm) than the diameter of the nanotubes 108.

The redox status (and thus the volume) of the electroactive polymer 112, and thus of the controllable organic membrane 36a, can be adjusted with the application of appropriate electrical stimulus. Preferably, the redox statuses, and thereby the volume of the electroactive polymer 112 and the controllable organic membrane 36a, is controlled by means of contacts between the conductive material and the control device 88. An increase in volume leads to closure of the nanopores 110 of the carrier structure 106 and the pores 72 of the controllable organic membrane 36a, while conversely, a decrease in volume causes the opening of the nanopores 110 and the pores 72 for acceptance of the analyte 30. Because the reduction or oxidation of the electroactive polymer 112 can occur partially, the opening of the nanopores 110 and the pores 72 can be continuously adjusted to a range of sizes, which in turn enables an adjustment to different analytes 30.

FIGS. 8A and 8B show a pore 72 in a closed state (FIG. 8A) and in an opened state (FIG. 8B). The electroactive polymer 112 incorporates a matrix 118 of crosslinked, positively charged fibers made of polypyrrole 114. During polymerization with the coating of the gold layer, negatively charged DBS molecules 116 become deposited in this matrix 118. Due to their size, these molecules are not able to diffuse out of the matrix 118 and represent negatively charged counterions to the positively charged matrix 118 of polypyrrole 114. With a full reduction of the polypyrrole 114, it becomes electrically neutral.

The pores 72 are closed in the following manner. To compensate for the negative charge of the DBS molecules 116, positively charged, hydrated sodium ions 120 are deposited in the matrix 118 by applying a voltage of 2 volts, for example. There, they lead to a strong (up to 30%) lateral volume change in the electroactive polymer 112. This change in volume leads to a closure of the pores 72 and prevents the entry of structures into the sample volume 60. The process can be reversed by applying a voltage of reverse polarity, which then leads to a reduction in the volume of the polymer 112. The reversibility of this process makes it possible to repeatably open and close the pores 72. Further, a partial volume change in the controllable organic membrane 36a is possible by means of the degree of reduction in the volume of the polymer 112. The respective redox statuses of the electroactive polymer 112 are produced by means of differently applied voltages, and can be maintained after the voltage is switched off.

With the controllable membrane 36a, which can be reversibly switched between an opened and a closed state of the reservoir 38, the sensor 14 can be both measuring sensor 80 and reference sensor 42. In this case, the membrane, as shown in FIG. 7A, is closed prior to a first measurement of the sensor system 10, but also between the various measurements, so that in this state neither the characteristic 12 or analyte 30 to be detected, nor other structures, are able to penetrate into the sample volume 60 or to escape from the volume.

To detect the characteristic 12, in a first step (FIG. 7B) the diameter of the pore 72 of the controllable organic membrane 36a is adjusted to a first diameter 86, and in a second step (FIG. 7C), the diameter of the pore 72 is adjusted to a second diameter 74, wherein the first diameter 86 is smaller than the second diameter 74. The first step represents a reference measurement step, in which as many interference signals as possible are to be detected. The first diameter 86 is adjusted such that the characteristic 12 or the analyte 30 cannot penetrate into the sample volume 60, and amounts to about 5 nm, for example. However, all smaller molecules 78 which could impair a determination of the analyte 30 can penetrate into the sample volume 60. The second step is an analyte measurement step in which the second diameter 74 is increased to (for example) about 10 nm for the measurement of cystatin C, or to 1 nm for the measurement of glucose, so that the analyte 30 is then able to penetrate into the sample volume 60 in order to be measured. These steps can be accomplished by applying different voltages of, for example, 1 V for the reference measurement and a voltage of 1.5 V for the analyte measurement. Alternatively, the diameter can be adjusted with the application of a constant applied voltage (for example, 2 V) in dependence on the duration of the applied voltage. Typical values are 4 minutes for the reference measurement and 5 minutes for the analyte measurement. To obtain a final measurement of the concentration of analyte 30, the result of the analyte measurement is then corrected by the result of the reference measurement.

It will be apparent to those skilled in the art that numerous modifications and variations of the described examples and versions of the invention are possible in light of the foregoing discussion. The described examples and versions are presented for purposes of illustration only, and it is the intent to cover all such modifications and alternate versions that come within the scope of the claims below, or which are legally equivalent thereto.

What is claimed is:

1. A medical sensor system (10, 10') for detecting a characteristic (12) of a human and/or animal body, the sensor system (10, 10') including:
   a. a characteristic carrier receptor (18) configured to bind to a second characteristic carrier (20) of interest for sensing;
   b. a first characteristic carrier (16):
      (1) different from the second characteristic carrier (20), and
      (2) configured to bind to the characteristic carrier receptor (18) in competition with the second characteristic carrier (20);
   c. a sensor (14) configured to generate a signal dependent on the binding of at least one of the first characteristic carrier (16) and the second characteristic carrier (20) to the characteristic carrier receptor (18);
   d. a reservoir (38) wherein the sensor (14) is situated, and
   e. an organic membrane (36, 36a) closing the reservoir (38), wherein the organic membrane (36, 36a):
      (1) always retains the first characteristic carrier (16) within the reservoir (38), and
      (2) is controllable to selectively allow and deny entry of the second characteristic carrier (20) into the reservoir (38).

2. The medical sensor system of claim 1 wherein the sensor (14) is configured to generate an electrical signal dependent on the binding of at least one of the first characteristic carrier (16) and the second characteristic carrier (20) to the characteristic carrier receptor (18).

3. The medical sensor system of claim 1 wherein the sensor (14) is configured to generate a voltage signal dependent on the binding of at least one of the first characteristic carrier (16) and the second characteristic carrier (20) to the characteristic carrier receptor (18).

4. The medical sensor system of claim 1 wherein the sensor (14) includes a semiconductor component (22) configured to generate the binding-dependent signal.

5. The medical sensor system of claim 4 wherein the semiconductor component (22) includes a gate (24) whereupon the characteristic carrier receptor (18) is located.

6. The medical sensor system of claim 1 wherein the sensor (14) includes a region (24) coated with the characteristic carrier receptor (18).

7. The medical sensor system of claim 6 further including a passivating layer (44) on the region (24) of the sensor (14), the passivating layer being configured to saturate non-specific binding sites (46).

8. The medical sensor system of claim 1 wherein the characteristic carrier receptor (18) is defined by a molecule having an antigen recognition site (26).

9. The medical sensor system of claim 1 wherein:
   a. the second characteristic carrier (20) is defined by an analyte (30) that has an antigen (28), and
   b. the first characteristic carrier (16) is defined by an antagonist (32) of the analyte (30).

10. The medical sensor system of claim 1 wherein the first characteristic carrier (16) has a higher charge (34) than the second characteristic carrier (20).

11. The medical sensor system of claim 1 wherein the organic membrane (36a) is electrically controllable.

12. The medical sensor system of claim 1 further including a reference sensor (44) configured to generate a background signal representative of the absence of the second characteristic carrier (20) from the reservoir (38).

13. The medical sensor system of claim 1 further including a surface coating (48) applied to the membrane (36, 36a), the surface coating (48) being configured to prevent interactions with interfering substances (52).

14. The medical sensor system of claim 1 wherein:
   a. the reservoir (38) is at least partially filled with fluid, and
   b. the first characteristic carrier (16) is dispersed throughout the fluid.

15. The medical sensor system of claim 1 further including a medical implant (54) whereupon or wherein the medical sensor system (10, 10') is situated.

16. The medical sensor system of claim 1 wherein the characteristic carrier receptor (18) includes at least a portion of a monoclonal antibody configured to bind to the first characteristic carrier (16) and the second characteristic carrier (20).

17. A method for operating the medical sensor system of claim 1 including the step of determining the change in the binding-dependent signal when the sensor (14) is located in vivo.

18. A medical sensor system for detecting a characteristic of a human and/or animal body, the sensor system including:
   a. a reservoir;
   b. a first characteristic carrier within the reservoir;
   c. a sensor within the reservoir, the sensor being configured to generate a signal dependent on the relative amounts of:
      (1) the first characteristic carrier adjacent the sensor, and
      (2) a second characteristic carrier adjacent the sensor,
   d. a membrane closing the reservoir, the membrane having a pore therein, the pore having a pore size which is controllable to selectively:
      (1) allow passage of the second characteristic carrier into the reservoir, and
      (2) prevent passage of the second characteristic carrier into the reservoir.

19. The medical sensor system of claim 18 wherein the pore size is electrically controllable.

20. A medical sensor system for detecting a characteristic of a human and/or animal body, the sensor system including:
   a. a reservoir;
   b. a characteristic carrier receptor within the reservoir, the characteristic carrier receptor being configured to competitively bind to:
      (1) a first characteristic carrier, and
      (2) a second characteristic carrier of interest for sensing,
   c. a membrane closing the reservoir, the membrane being configured to:
      (1) restrain the first characteristic carrier within the reservoir, and
      (2) selectively allow entry of the second characteristic carrier into the reservoir in response to a control signal;
   d. a sensor configured to generate a signal dependent on the amount of at least one of the first characteristic carrier and the second characteristic carrier bound to the characteristic carrier receptor.

21. The medical sensor system of claim 20, wherein the membrane having a pore therein, the pore size being electrically controllable.

* * * * *